United States Patent [19]

Bucher et al.

[11] 4,448,776

[45] May 15, 1984

[54] METHOD OF USING CERTAIN SUBSTITUTED ALIPHATIC SECONDARY AMINES OR THEIR SALTS FOR EASING BREATHING

[76] Inventors: Karl Bucher, Wielandplatz 2, 5054 Basel; Max Matter, Lindenweg 3, 4052 Basel; Bernhard Brunner, Seegarten, 3626 Hünibach; Alfred Frey, Obere Hauptgasse 8, 3600 Thun, all of Switzerland

[21] Appl. No.: 341,035

[22] Filed: Jan. 20, 1982

[30] Foreign Application Priority Data

Feb. 12, 1981 [CH] Switzerland ............................ 939/81
May 10, 1981 [CH] Switzerland .......................... 6376/81

[51] Int. Cl.³ .................. A61K 31/24; A61K 31/135; A61K 31/495
[52] U.S. Cl. .................................... 424/250; 424/309; 424/330
[58] Field of Search .................... 424/330, 250, 309; 564/316, 321

[56] References Cited

U.S. PATENT DOCUMENTS

| | | | |
|---|---|---|---|
| 2,483,434 | 10/1949 | Rieveschl | 564/321 X |
| 2,627,491 | 2/1953 | Szabo et al. | 424/330 |
| 3,013,020 | 12/1961 | Fancher | 424/330 |
| 3,401,224 | 9/1968 | Barrett et al. | 424/250 |
| 3,483,209 | 12/1969 | Mizzoni | 424/330 |
| 3,501,527 | 3/1970 | Little et al. | 424/330 |
| 3,551,492 | 12/1970 | Mizzoni | 260/570.9 |
| 3,876,702 | 4/1975 | Petersen et al. | 564/316 |
| 4,010,282 | 3/1977 | Binnig et al. | 424/330 |
| 4,091,220 | 5/1978 | Ishiguro et al. | 424/248.54 |
| 4,153,794 | 5/1979 | Ishiguro et al. | 564/358 |

FOREIGN PATENT DOCUMENTS

| | | |
|---|---|---|
| 752331 | 7/1956 | United Kingdom . |
| 786215 | 11/1957 | United Kingdom . |
| 863217 | 3/1961 | United Kingdom . |
| 872371 | 7/1961 | United Kingdom . |
| 987438 | 3/1965 | United Kingdom . |
| 1025041 | 4/1966 | United Kingdom . |
| 1109502 | 4/1968 | United Kingdom . |
| 1405767 | 9/1975 | United Kingdom . |
| 2084019 | 4/1982 | United Kingdom . |

OTHER PUBLICATIONS

Bucher et al.–Agents & Actions, vol. 3, No. 1 (1973), pp. 28–34 (Switzerland).

*Primary Examiner*—Leonard Schenkman
*Attorney, Agent, or Firm*—Heinrich W. Herzfeld

[57] ABSTRACT

Compounds of the formula I $$R_1-CH(R_2)-N(R_3)-R_4 \qquad (I)$$

in which $R_1$ is unsubstituted or substituted phenyl, $R_2$ is hydrogen lower alkyl, unsubstituted or substituted phenyl or free or esterified carboxy, and in which $R_3$ is hydrogen or lower alkyl and $R_4$ is a group of the formula $-alk_1-X-alk_2-R_5$, or $R_3$ and $R_4$ together are a group of the formula $-alk_3-NH-alk_4-$, $alk_1$ and $alk_2$ being lower alkylidene, $alk_3$ and $alk_4$ lower alkylene, X a direct bond, methylene or unsubstituted or substituted phenylene and $R_5$ being hydroxy, amino or substituted amino of the formula $-N(R_6)-CH(R_7)-R_8$ in which $R_6$ is hydrogen, or, provided that $R_3$ is hydrogen, it may alternatively be lower alkyl or unsubstituted or substituted phenyl-lower alkyl, $R_7$ is hydrogen, lower alkyl, unsubstituted or substituted phenyl or free or esterified carboxy and $R_8$ is unsubstituted or substituted phenyl, and their pharmaceutically acceptable salts have properties that ease breathing and are suitable for combating respiratory disorders, preferably as active ingredients in and/or for the manufacture of pharmaceutical preparations that ease breathing.

21 Claims, No Drawings

METHOD OF USING CERTAIN SUBSTITUTED ALIPHATIC SECONDARY AMINES OR THEIR SALTS FOR EASING BREATHING

The invention relates to the use of compounds of the formula I

$$R_1-CH(R_2)-N(R_3)-R_4 \qquad (I)$$

in which $R_1$ is unsubstituted or substituted phenyl, $R_2$ is hydrogen, lower alkyl, unsubstituted or substituted phenyl or free or esterified carboxy, and in which $R_3$ is hydrogen or lower alkyl and $R_4$ is a group of the formula $-alk_1-X-alk_2-R_5$, or $R_3$ and $R_4$ together are a group of the formula $-alk_3-NH-alk_4-$, $alk_1$ and $alk_2$ being lower alkylidene, $alk_3$ and $alk_4$ lower alkylene, X a direct bond, methylene or unsubstituted or substituted phenylene and $R_5$ being hydroxy, amino or substituted amino of the formula $-N(R_6)-CH(R_7)-R_8$ in which $R_6$ is hydrogen, or, provided that $R_3$ is hydrogen, it may alternatively be lower alkyl or unsubstituted or substituted phenyl-lower alkyl, $R_7$ is hydrogen, lower alkyl, unsubstituted or substituted phenyl or free or esterified carboxy and $R_8$ is unsubstituted or substituted phenyl, and their pharmaceutically acceptable salts for combating respiratory disorders, for example as the active ingredient in and/or for the manufacture of pharmaceutical preparations that ease breathing, and pharmaceutical preparations that ease breathing and that contain those compounds or salts.

As seen from the above proviso definition of $alk_1$ and $alk_2$, the methylene group is considered herein to be the lowest member of the alkylidene series as well as of the alkylene series.

The invention also relates to compounds of the formula I in which $R_1$, $R_2$, $R_3$, $R_4$, $R_5$, $R_6$, $R_7$, $R_8$, $alk_1$, $alk_2$, X, $alk_3$ and $alk_4$ have the meanings given above with the proviso, in compounds in which $R_3$ is hydrogen or lower alkyl, $R_4$ is a group $-alk_1-X-alk_2-R_5$ and $R_5$ is a group $-N(R_6)-CH(R_7)-R_8$, that, when X is unsubstituted or substituted phenylene, at least one of the radicals $R_1$ and $R_8$ is different from unsubstituted or N-substituted aminoalkoxyphenyl or at least one of the radicals $R_2$, $R_6$ and $R_7$ is different from hydrogen and lower alkyl, and, when $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine or at least one of the radicals $R_2$, $R_3$, $R_6$ and $R_7$ is different from hydrogen, and and with the further proviso, in compounds in which $R_3$ and $R_4$ together are a group $-alk_3-NH-alk_4-$ and $alk_3$ is is ethylene, that, when $alk_4$ is ethylene, $R_1$ is different from unsubstituted phenyl or $R_2$ is different from unsubstituted phenyl and hydrogen and, furthermore, $R_1$ is different from 2,3,4-trimethoxyphenyl, o-aminodichlorophenyl, o-acylaminodichlorophenyl and o-diacylaminodichlorophenyl or $R_2$ is different from hydrogen, and, when $alk_4$ is 1,3-propylene, $R_1$ is different from unsubstituted phenyl or $R_2$ is different from hydrogen, wherein, in the case where $R_4$ is a group $-alk_1-X-alk_2-R_5$ and $alk_1$ and $alk_2$ are methylene and $R_5$ is a group of the formula $-N(R_6)-CH(R_7)-R_8$, $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, hydroxy, chlorine, diethylamino, dimethylamino and/or nitro when $R_2$, $R_3$, $R_6$ and $R_7$ are hydrogen and X is methylene, and $R_1$ and $R_8$ are different radicals selected from p-aminophenoxyphenyl and p-nitrophenoxyphenyl when $R_2$ and $R_7$ are hydrogen and $R_3$ and $R_6$ are hydrogen or lower alkyl and X is methylene or a direct bond, and their pharmaceutically acceptable salts, with the proviso that acid addition salts with organic carboxylic acids do not have a β-lactam ring in the anion, for use in a process for the therapeutic treatment of the human or animal body, pharmaceutical preparations containing them and their use for combating diseases, or as the active ingredient in or for the manufacture of pharmaceutical preparations.

The invention likewise relates to compounds of a general formula IA, similar to the formula I in which $R_1$ and $R_2$ have the meanings given above, $R_3$ is hydrogen or lower alkyl and $R_4$ is a group of the formula $-alk_1-X-alk_2-N(R_6)-CH(R_7)-R_8$ in which $alk_1$, X, $alk_2$, $R_6$, $R_7$ and $R_8$ have the meanings given above, with the proviso that, in compounds of the formula IA in which X is unsubstituted or substituted phenylene, at least one of the radicals $R_1$ and $R_8$ is different from unsubstituted or N-substituted aminoalkoxyphenyl when $R_2$, $R_6$ and $R_7$ are hydrogen or lower alkyl, also that, in compounds of the formula IA in which $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine and from p-hydroxyphenyl when $R_2$, $R_3$, $R_6$ and $R_7$ are hydrogen, and with the further proviso, in compounds of the formula IA in which $alk_1$ and $alk_2$ are methylene and X is a direct bond, that, when both radicals $R_2$ and $R_7$ are hydrogen or both are unsubstituted phenyl or both are methyl or both are ethyl and $R_7$ is hydrogen, at least one of the radicals $R_1$ and $R_8$ is different from unsubstituted phenyl or at least one of the radicals $R_3$ and $R_6$ is different from hydrogen, wherein $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, hydroxy, chlorine, diethylamino, dimethylamino and/or nitro when $R_2$, $R_3$, $R_6$ and $R_7$ are hydrogen and X is methylene, $R_1$ and $R_8$ can further be different substituents selected from p-anilino, p-hydroxyphenyl and p-methylphenyl when $R_2$, $R_3$, $R_6$ and $R_7$ are hydrogen and X is a direct bond, and $R_1$ and $R_8$ are different radicals selected from p-aminophenoxyphenyl and p-nitrophenoxyphenyl when $R_2$ and $R_7$ are hydrogen and $R_3$ and $R_6$ are hydrogen or lower alkyl and X is methylene or a direct bond, and their salts and processes for their manufacture.

Phenylene is preferably 1,3- or 1,4-phenylene but may alternatively be 1,2-phenylene.

There come into consideration as substituents of phenyl and phenyl in phenyl-lower alkyl and also of phenylene, for example, aliphatic and cycloaliphatic radical, free or etherified or free or esterified hydroxy, unsubstituted or substituted amino, nitro and/or trifluoromethyl.

Esterified carboxy is, for example, aliphatically or cycloaliphatically esterified carboxy, such as unsubstituted or substituted lower alkoxycarbonyl or lower alkenyloxy- or lower alkynyloxy-carbonyl or 3- to 8-membered cycloalkoxy-carbonyl.

Aliphatic radicals are, for example, aliphatic hydrocarbon radicals that are unsubstituted or substituted by hydroxy, lower alkoxy or lower alkanoyloxy, such as lower alkyl, lower alkenyl, lower alkynyl, mono- or di-hydroxy-lower alkyl, lower alkoxy-lower alkyl or lower alkanoyloxy-lower alkyl.

Cycloaliphatic radicals are, for example, 3- to 8-membered cycloalkyl radicals.

Araliphatic radicals are, for example, phenyl-lower alkyl radicals that are unsubstituted or substituted as indicated for phenyl but are preferably phenyl-lower alkyl radicals that are unsubstituted or substituted by lower alkyl, lower alkoxy, halogen and/or trifluoromethyl.

Free or etherified or free or esterified hydroxy is, for example, hydroxy etherified by an unsubstituted or substituted aliphatic alcohol, such as lower alkoxy, lower alkenyloxy, lower alkynyloxy, mono- or di-hydroxy-lower alkoxy, lower alkoxy-lower alkoxy, lower alkanoyl-lower alkoxy or lower alkyl(id)enedioxy bonded to adjacent carbon atoms, or hydroxy esterified by a hydrohalic acid or an organic carboxylic acid, such as halogen, lower alkanoyloxy, or benzoyloxy that is unsubstituted or substituted as indicated for phenyl, but that is preferably unsubstituted or substituted by lower alkyl, lower alkoxy, halogen and/or trifluoromethyl.

Unsubstituted or substituted amino is, for example, unsubstituted or aliphatically substituted amino, such as amino, mono- or di-lower alkylamino or lower alkyleneamino, or acylamino, such as mono- or di-lower alkanoylamino, or benzoylamino that is unsubstituted or substituted as indicated for phenyl but that is preferably unsubstituted or substituted by lower alkyl, lower alkoxy, halogen and/or trifluoromethyl.

Lower alkyl is, for example, methyl, ethyl, n-propyl, isopropyl, n-butyl, isobutyl, sec-butyl, tert-butyl, pentyl, hexyl or heptyl.

Lower alkenyl is, for example, vinyl, allyl, methallyl and crotyl.

Phenyl-lower alkyl is, for example, benzyl, 2-phenylethyl, 2- or 3-phenylpropyl or triphenylmethyl.

3- to 8-membered cycloalkyl is, for example, cyclopropyl, cyclopentyl, cyclohexyl or cycloheptyl.

Mono- and di-hydroxy-lower alkyl is, for example, 1- or 2-hydroxyethyl, 1-, 2- or 3-hydroxypropyl, 1,2-dihydroxyethyl or 1,2-dihydroxypropyl.

Lower alkoxy-lower alkyl is, for example, methoxyethyl, 2-ethoxyethyl, 3-methoxypropyl, 3-ethoxypropyl or 1,2-dimethoxyethyl.

Lower alkanoyloxy-lower alkyl is, for example, acetoxymethyl, 2-acetoxyethyl or pivaloyloxymethyl.

Lower alkoxy is, for example, methoxy, ethoxy, n-propoxy, isopropoxy, n-, sec-, iso- or tert-butoxy, and pentyloxy, hexyloxy or heptyloxy.

Lower alkenyloxy is, for example, allyloxy or methallyloxy.

Lower alkynyloxy is, for example, propargyloxy.

Mono- or di-hydroxy-lower alkoxy is, for example, hydroxyethoxy, 2- or 3-hydroxypropoxy, hydroxyisopropoxy, 2,3-dihydroxypropoxy or 1,3-dihydroxy-2-propoxy.

Lower alkoxy-lower alkoxy is, for example, methoxymethoxy, 2-methoxyethoxy, 2-ethoxyethoxy or 3-methoxypropoxy.

Lower alkyl(id)enedioxy is, for example, methylenedioxy, ethylenedioxy, 1,3-propylenedioxy and isopropylidenedioxy.

Lower alkanoyl-lower alkoxy is, for example, acetylmethoxy, acetylethoxy or pivaloylethoxy.

Lower alkanoyloxy is, for example, acet-, propionyl-, butyryl-, isobutyryl- or pivaloyl-oxy.

Lower alkoxycarbonyl is, for example, methoxycarbonyl, ethoxycarbonyl, n-propoxycarbonyl or tert-butoxycarbonyl.

Lower alkenyloxycarbonyl is, for example, methallyl- or allyloxycarbonyl.

Lower alkynyloxycarbonyl is, for example, propargyloxycarbonyl.

3- to 8-membered cycloalkoxycarbonyl is, for example, cyclopentyloxycarbonyl, cyclohexyloxycarbonyl or cycloheptyloxycarbonyl, also cyclopropoxycarbonyl.

Mono- or di-lower alkylamino is, for example, methylamino, ethylamino, n-butylamino, dimethylamino or diethylamino.

Lower alkyleneamino is, for example, pyrrolidin-1-yl or piperidino.

Mono- or di-lower alkanoylamino is, for example, formylamino, acetylamino, diacetylamino or succinimino.

Halogen is, for example, halogen having an atomic number of up to and including 35, such as fluorine, chlorine or bromine.

The compounds of the formula I can form isomers, for example they may be in the form of an optical isomer, for example, depending on the number of asymmetric carbon atoms, they may be in the form of enantiomers or diastereoisomers, or in the form of mixtures of the same, for example racemates or mixtures of diastereoisomers.

Salts of compounds of the formula I are, for example, the pharmaceutically acceptable acid addition salts thereof, also pharmaceutically acceptable salts of compounds of the formula I that contain carboxy and/or phenolic hydroxy groups, with bases, also internal salts of compounds of the formula I that contain carboxy. Acid addition salts are, for example, pharmaceutically acceptable addition salts with inorganic acids, such as hydrohalides, for example hydrochlorides or hydrobromides, bisulphates, phosphates, borates and the like, also pharmaceutically acceptable addition salts with organic acids, provides that salt-forming organic carboxylic acids do not have a β-lactam ring, especially acid addition salts with open-chain or carbocyclic organic acids, such as aliphatic carboxylic acids that are non-hydroxylated or hydroxylated, such as lower alkane-mono- or -di-carboxylic acid salts, for example acetates, malonates or succinates, lower alkene-mono- or -di-carboxylic acid salts, for example fumarates or maleates, oxo- or hydroxy-lower alkanedicarboxylic acid salts, such as pyruvates, tartrates, malates and the like, also salts with organic sulphonic acids, such as aliphatic or aromatic sulphonic acid salts, for example methanesulphonates, benzenesulphonates, p-toluenesulphonates and the like, sulphamates, for example N-cyclohexylsulphamates, or salts with 3,7-dihydro-1H-purine-2,6-diones that are unsubstituted or 1-, 3- and/or 8-substituted, for example with 8-chloro-3,7-dihydro-1,3-dimethyl-1H-purine-2,6-dione. Pharmaceutically acceptable base salts are, for example, alkali metal or alkaline earth metal salts, for example sodium, potassium, magnesium or calcium salts, and, in the case of compounds of the formula I containing carboxy, also ammonium salts with ammonia or organic amines, such as mono-, di- and tri-lower alkylamines, for example ethyl-, diethyl- or trimethylamine, or mono-, di- and tri-(hydroxy-lower alkyl)-amines, for example ethanolamine or di- or tri-ethanolamine.

Some of the compounds of the formula I are known and are proposed predominantly as intermediates for the manufacture of fine chemicals having various uses. Some, however, are also known to have pharmacological properties on the basis of which they can be used as the active ingredient of medicaments, for example in antihistamines, spasmolysants, antiarrythmic agents and antidepressants. According to German Offenlegungsschrift No. 2 551 355, a narrowly defined group of compounds of the formula I, namely those in which $R_1$ is phenyl substituted in the o-position by amino, mono- or di-acylamino and additionally by 2 chlorine atoms, $R_2$ is hydrogen and $R_3$ and $R_4$ together are a group of the formula $-CH_2CH_2NHCH_2CH_2-$, possess, in addition, properties that stimulate the fluid secretion of the respiratory tract and they have been proposed, inter alia, as expectorants.

The invention is based on the surprising discovery that the compounds of the formula I and their pharmaceutically acceptable salts have properties that ease breathing to a marked extent. Thus, they increase respiratory capacity without generally significantly increasing respiratory frequency. In this respect, the compounds of the formula I differ essentially from the so-called respiratory stimulants, such as, N,N-diethylpyridine-3-carboxamide (nikethamide) and the combination (prethcamide) of N-ethyl-N-(1-dimethylcarbamoylpropyl)-crotonamide (crotethamide) and N-propyl-N-(1-dimethylcarbamoylpropyl)-crotonamide (cropropamide), the effect of which on respiratory capacity consists especially in an increase in respiratory frequency. Only α-phenyl-α-(2-piperidinyl)-methyl acetate (methyl phenidate) is known to have a similar action. This compound, however, like the above-mentioned respiratory stimulants, belongs to a completely different class of substances. It also has pronounced, and not in all cases desirable, effects of stimulating the central nervous system and also undesirable properties.

The properties of easing breathing possessed by the compounds of the formula I and their salts can be demonstrated in tests on animals, for example the test arrangement according to Agents and Actions 3, 28–34 (1973).

According to this arrangement, both male and female rabbits weighing from 2 to 3 kg are narcotised with ethylurethane (1.2 g/kg s.c.) and bound in the supine position and a tracheotomy tube is introduced. The respiratory activity is recorded on the basis of the pleural pressure ($P_{pl}$). The trachea is closed every 20 minutes and kept closed for 30 seconds. The first closure of the trachea gives the normal individual respiratory capacity value. 3 minutes before each subsequent closure of the trachea, an aqueous solution of the test substance is administered intravenously in the course of 60 seconds. After each measurement the dose is increased by a factor of 3, the starting dose being such that the lethal dose ($D_1$) is reached at approximately the 7th administration. To establish actual effectiveness, for the entire period during which the trachea is closed the average pleural negative pressure during inspiration and expiration, including the following pause ($\bar{p}_i$), the maximum pleural negative pressure developed during attempts to breathe in ($p_i^{max}$) and the respiratory frequency ($f_r$) are measured for each breath. All three parameters are then averaged out over the entire period during which the trachea is closed. The increasing effect of the test substance on respiratory capacity is demonstrated in an increase in the average pleural negative pressure ($\Delta \bar{p}_i$) and in the maximum pleural negative pressure ($\Delta p_i^{max}$) compared with the normal value which is set at 100%.

In this test, the values listed in the following Table were established for the increase obtainable in the average and maximum pleural negative pressures ($\Delta \bar{p}_i$) and ($\Delta p_i^{max}$), respectively, and the change in respiratory frequency ($\Delta f_r$) and also for the minimum dose at which the $\bar{p}_i$ significantly increases ($D_e$ in g/kg) and the lethal dose ($D_1$ in g/kg):

| Test substance | $\Delta \bar{p}_i$ | $\Delta p_i^{max}$ | $\Delta f_r$ | $D_e$ | $D_1$ |
|---|---|---|---|---|---|
| I*[a] | 4% | 14% | +5% | 0.003 | over 0.01 |
| II*[a] | 10% | 0% | 0% | 0.002 | over 0.04 |
| III*[a] | 17% | 3% | +2% | 0.0005 | 0.01 |
| IV*[a] | 20% | 27% | +5% | 0.0002 | 0.002 |
| V*[a] | 13% | 21% | +2% | 0.001 | 0.04 |
| VI*[a] | 7% | 11% | +1% | 0.002 | over 0.01 |
| VII*[a] | 13% | 23% | +1% | 0.003 | 0.1 |
| VIII*[a] | 13% | 10% | +3% | 0.001 | 0.03 |
| IX*[a] | 18% | 16% | +3% | 0.002 | 0.03 |
| X*[a] | 14% | 28% | −9% | 0.001 | 0.01 |
| XI*[a] | 11% | 9% | −3% | 0.005 | over 0.01 |
| XII*[a] | 9% | 2% | +7% | 0.001 | 0.03 |
| XIII*[a] | 18% | 19% | +1% | 0.002 | 0.03 |
| XIV*[b] | 29% | 12% | +2% | 0.002 | 0.04 |
| XV*[a] | 9% | 11% | 0 | 0.003 | over 0.01 |
| XVI*[a] | 15% | 5% | +15% | 0.015 | over 0.04 |
| XVII*[a] | 20% | 20% | +5% | 0.002 | over 0.01 |
| XVIII[a] | 12% | 4% | +11% | 0.003 | 0.03 |
| XIX*[a] | 25% | 17% | +9% | 0.002 | 0.02 |
| methyl phenidate[c] | 17% | 9% | −1% | 0.003 | 0.05 |
| nikethamide | 19% | 12% | +84% | 0.1 | 0.3 |
| prethcamide | 5% | 2% | +15% | 0.1 | over 0.1 |
| strychnine | 2% | 6% | −4% | 0.0001 | 0.003 |

[a] = administered as bis-methanesulphonate,
[b] = administered as methanesulphonate,
[c] = administered as hydrochloride.

The effect of the compounds of the formula I of easing breathing was confirmed in human beings in a preliminary clinical trial using a selected compound. For example, with 4 test persons the following observations were made after administering N,N'-bis-(diphenylmethyl)-1,2-propylenediamine (V*,).

Test person 1: (male, age 73, pulmonary emphysema) was given p.o. 10 mg of active ingredient. 1 hour later the vital capacity (VC) and the forced expiratory volume at 1 second ($FEV_{1,0}$) were 3.3 l and 2.7 l compared with 2.5 l and 2.1 l as the starting values. No side effects were observed.

Test person 2: (male, age 77, pulmonary emphysema and pulmonary heart disease) was given i.v. 10 mg of active ingredient in the form of an aqueous solution of bis-methanesulphonate. 1 hour later the vital capacity (VC) and the forced expiratory volume at 1 second ($FEV_{1,0}$) were 2.5 l and 2.4 l compared with 2.1 l and 2.0 l as the starting values. No side effects were observed.

Test person 3: (male, age 72, pulmonary emphysema) suffering from dyspnea was given, p.o. in a placebo test, a placebo and 10 mg of active ingredient. 2 hours after the administration of the placebo the vital capacity (VC) and the forced expiratory volume at 1 second ($FEV_{1,0}$) were 2.1 l and 1.3 l compared with 2.1 l and 1.2 l as the starting values; the subjective condition was unchanged. 2 hours after the administration of the active ingredient, the vital capacity (VC) and the forced expiratory volume at 1 second ($FEV_{1,0}$) were 2.6 l and 1.25 l compared with 2.2 l and 1.2 l and the test person stated that he could breathe "more easily" and felt stronger.

Test person 4: (male, age 84, pulmonary emphysema) suffering from dyspnea was given 10 mg of active ingredient and a placebo in a placebo test. 2 hours after the administration of the active ingredient the vital capacity (VC) and the forced expiratory volume at 1 second ($FEV_{1,0}$) were 1.85 l and 1.0 l compared with 1.6 l and 0.7 l. The test person stated that he could breathe "more easily and freely". 2 hours after the administration of the placebo the vital capacity (VC) and the forced expiratory volume at 1 second ($FEV_{1,0}$) were 1.65 l and 0.75 l compared with 1.6 l and 0.7 l, and the subjective condition was unchanged.

Because of their specific action of increasing respiratory capacity, the compounds of the formula I are accordingly suitable as the active ingredients of medicaments in pharmaceutical preparations that ease breathing, for the prophylactic and therapeutic influencing of respiratory disorders of the most varied origins, especially respiratory disorders caused by old age. They may, however, also be used for the controlled increase of respiratory capacity, for example in the case of unfavourable respiratory conditions.

The invention relates especially to the use of compounds of the formula IC

$$R_1-CH(R_2)-N(R_3)-R_4 \qquad (IC)$$

in which $R_1$ is unsubstituted phenyl or phenyl substituted by aliphatic, cycloaliphatic or araliphatic radicals, by hydroxy, etherified or esterified hydroxy, unsubstituted or aliphatically substituted amino, acylamino, nitro and/or by trifluoromethyl, $R_2$ is hydrogen, lower alkyl, unsubstituted phenyl or phenyl substituted by aliphatic, cycloaliphatic or araliphatic radicals, by hydroxy, etherified or esterified hydroxy, unsubstituted or aliphatically substituted amino, acylamino, nitro and/or by trifluoromethyl, or is aliphatically, cycloaliphatically or araliphatically esterified carboxy, and in which $R_3$ is hydrogen or lower alkyl and $R_4$ is a group of the formula $-alk_1-X-alk_2-R_5$ or $R_3$ and $R_4$ together are a group of the formula $-alk_3-NH-alk_4-$, wherein $alk_1$ and $alk_2$ are lower alkylidene, $alk_3$ and $alk_4$ are lower alkylene, X is a direct bond, methylene or unsubstituted phenylene or phenylene substituted by aliphatic, cycloaliphatic or araliphatic radicals, by hydroxy, etherified or esterified hydroxy, unsubstituted or aliphatically substituted amino, acylamino, nitro and/or by trifluoromethyl, $R_5$ is hydroxy, amino or substituted amino of the formula $-N(R_6)-CH(R_7)-R_8$ in which $R_6$ is hydrogen or, provided that $R_3$ is hydrogen, it may alternatively be lower alkyl or unsubstituted phenyl-lower alkyl or phenyl-lower alkyl substituted by aliphatic, cycloaliphatic or araliphatic radicals, by hydroxy, etherified or esterified hydroxy, unsubstituted or aliphatically substituted amino, acylamino, nitro and/or by trifluoromethyl, $R_7$ is hydrogen, lower alkyl, unsubstituted phenyl or phenyl substituted by aliphatic, cycloaliphatic or araliphatic radicals, by hydroxy, etherified or esterified hydroxy, unsubstituted or aliphatically substituted amino, acylamino, nitro and/or by trifluoromethyl or is aliphatically, cycloaliphatically or araliphatically esterified carboxy, and $R_8$ is unsubstituted phenyl or phenyl substituted by aliphatic, cycloaliphatic or araliphatic radicals, by hydroxy, etherified or esterified hydroxy, unsubstituted or aliphatically substituted amino, acylamino, nitro and/or by trifluoromethyl, and their pharmaceutically acceptable salts for combating respiratory disorders, for example as the active ingredient in and/or for the manufacture of pharmaceutical preparations that ease breathing and also pharmaceutical preparations that ease breathing and that contain those compounds or salts.

The invention also relates especially to compounds of the formula I in which $R_1$, $R_2$, $R_3$, $R_4$, $R_5$, $R_6$, $R_7$, $R_8$, $alky_1$, $alk_2$, X, $alk_3$ and $alk_4$ have the meanings given above with the proviso that $R_3$ is hydrogen or lower alkyl, $R_4$ is a group $-alk_1-X-alk_2-R_5$ and $R_5$ is a group $-N(R_6)-CH(R_7)-R_8$, that, when X is unsubstituted phenylene or phenylene substituted as indicated, at least one of the radicals $R_1$ and $R_8$ is different from unsubstituted or N-substituted aminoalkoxyphenyl or at least one of the radicals $R_2$, $R_3$, $R_6$ and $R_7$ is different from hydrogen or lower alkyl, and that, when $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine or at least one of the radicals $R_2$, $R_3$, $R_6$ and $R_7$ is different from hydrogen, and with the further proviso, in compounds in which $R_3$ and $R_4$ together are a group $-alk_3-NH-alk_4-$ and $alk_3$ is ethylene, that, when $alk_4$ is ethylene, $R_1$ is different from unsubstituted phenyl or $R_2$ is different from unsubstituted phenyl and hydrogen and also $R_1$ is different from 2,3,4-trimethoxyphenyl, o-aminodichlorophenyl, o-acylaminodichlorophenyl and o-diacylaminodichlorophenyl or $R_2$ is different from hydrogen, and that, when $alk_4$ is 1,3-propylene, $R_1$ is different from unsubstituted phenyl or $R_2$ is different from hydrogen, wherein, in the case where $R_4$ is a group $-alk_1-X-alk_2-R_5$ and $alk_1$ and $alk_2$ are methylene and $R_5$ is a group of the formula $-N(R_6)-CH(R_7)-R_8$, $R_1$ and $R_8$ are different substituents selected from phenyl radicals that are unsubstituted or mono-, di-, tri- or tetra-substituted in the 3, 4-, 5- and/or 6-position(s) by isopropyl, methoxy, hydroxy, chlorine, diethylamino and/or dimethylamino when $R_2$, $R_3$, $R_6$ and $R_7$ are hydrogen and X is methylene, and $R_1$ and $R_8$ are different radicals selected from p-aminophenoxyphenyl and p-nitrophenoxyphenyl when $R_2$ and $R_7$ are hydrogen and $R_3$ and $R_6$ are hydrogen or lower alkyl and X is methylene or a direct bond, and their pharmaceutically acceptable salts, with the proviso that acid addition salts with organic carboxylic acids do not have a β-lactam ring in the anion, for use in a method for the therapeutic treatment of the human or animal body, pharmaceutical preparations containing them and their use for combating diseases or as the active ingredient in or for the manufacture of pharmaceutical preparations.

The invention likewise relates especially to compounds of the formula 1 in which $R_1$ and $R_2$ have the meanings given above, $R_3$ is hydrogen or lower alkyl and $R_4$ is a group of the formula $-alk_1-X-alk_2-N(R_6)-CH(R_7)-R_8$ in which $alk_1$, X, $alk_2$, $R_6$, $R_7$ and $R_8$ have the meanings given above, with the proviso that, in compounds of the formula I in which X is unsubstituted phenylene or phenylene substituted as indicated, at least one of the radicals $R_1$ and $R_8$ is different from unsubstituted or N-substituted aminoalkoxyphenyl when $R_2$, $R_3$, $R_6$ and $R_7$ are hydrogen or lower alkyl, further that, in compounds in which $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine and from p-hydroxyphenyl, when $R_2$, $R_3$, $R_6$ and $R_7$ are hydrogen, and with the further proviso, in compounds in which $alk_1$ and $alk_2$ are methylene and X is a direct bond, that, when both radicals $R_2$ and $R_7$ are hydrogen, or both are unsubstituted phenyl or both are methyl or $R_2$ is ethyl and $R_7$ is hydrogen, at least one of the radicals $R_1$ and $R_8$ is different from unsubstituted phenyl or at least one of the radicals $R_3$ and $R_6$ is different from hydrogen, wherein $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, hydroxy, chlorine, diethylamino and/or dimethylamino or are mono- or disubstituted in the 4- and/or 6-position by chlorine and/or nitro when $R_2$, $R_3$, $R_6$ and $R_7$ are hydrogen and X is methylene, $R_1$ and $R_8$ are different substituents selected from p-anilino, p-hydroxyphenyl and p-methylphenyl when $R_2$, $R_3$, $R_6$ and $R_7$ are hydrogen and X is a direct bond, and $R_1$ and $R_8$ are different radicals selected from p-aminophenoxyphenyl and p-nitrophenoxyphenyl when $R_2$ and $R_7$ are hydrogen and $R_3$ and $R_6$ are hydrogen or lower alkyl and X is methylene or a direct bond, and their salts, preferably pharmaceutically acceptable acid addition salts, and processes for their manufacture.

The invention relates more especially to the use of compounds of the formula I in which $R_1$ is unsubstituted phenyl or phenyl substituted by lower alkyl, such as methyl, lower alkenyl, such as vinyl or allyl, lower alkynyl, such as propargyl, mono- or di-hydroxy-lower alkyl, such as hydroxymethyl or 2-hydroxyethyl, lower alkoxy-lower alkyl, such as ethoxymethyl, lower alkanoyloxy-lower alkyl, such as acetoxymethyl or 2-acetoxyethyl, 3- to 8-membered cycloalkyl, such as cyclohexyl, hydroxy, lower alkoxy, such as methoxy, lower alkenyloxy, such as allyloxy, lower alkynyloxy, such as propargyloxy, mono- or di-hydroxy-lower alkoxy, such as 2-hydroxyethoxy, lower alkoxy-lower alkoxy, such as 2-methoxyethoxy, lower alkyl(id)enedioxy bonded to adjacent carbon atoms, such as ethylenedioxy or 2,2-propylenedioxy, halogen having an atomic number of up to and including 35, such as chlorine, lower alkanoyloxy, such as acetoxy, amino, mono- or di-lower alkylamino, such as methyl- or dimethyl-amino, and/or by mono- or di-lower alkanoylamino, such as acetylamino or diacetylamino, $R_2$ is hydrogen, lower alkyl, unsubstituted phenyl or phenyl substituted as indicated for $R_1$, lower alkoxycarbonyl, such as methoxy- or ethoxy-carbonyl, or 3- to 8-membered cycloalkoxycarbonyl, such as cyclohexyloxycarbonyl, $R_3$ is hydrogen, lower alkyl or phenyl-lower alkyl, such as methyl, and $R_4$ is a group of the formula —$alk_1$—X—$alk_2$—$R_5$, or $R_3$ and $R_4$ together are a group of the formula —$alk_3$—NH—$alk_4$—, wherein $alk_1$ and $alk_2$ are lower alkylidene, such as methylene, $alk_3$ and $alk_4$ are lower alkylene, such as ethylene or 1,3-propylene, X is methylene, a direct bond or unsubstituted phenylene or phenylene substituted by lower alkyl, such as methyl, lower alkoxy, such as methoxy, halogen and/or by trifluoromethyl, $R_5$ is hydroxy, amino or substituted amino of the formula —N($R_6$)—CH($R_7$)—$R_8$, $R_6$ is hydrogen or, provided that $R_3$ is hydrogen, may alternatively be lower alkyl, such as methyl, $R_7$ is hydrogen, lower alkyl, such as methyl, or unsubstituted phenyl or phenyl substituted as indicated for $R_2$, lower alkoxycarbonyl, such as methoxy- or ethoxycarbonyl, or 3- to 8-membered cycloalkoxycarbonyl, such as cyclohexyloxycarbonyl, and $R_8$ is unsubstituted phenyl or phenyl substituted as indicated for $R_1$, and their pharmaceutically acceptable acid addition salts or base salts for combating respiratory disorders, for example as the active ingredient in or for the manufacture of medicaments that ease breathing, and also preparations that ease breathing and that contain those compounds or salts.

The invention also relates more especially to compounds of the formula I in which $R_1$, $R_2$, $R_3$, $R_4$, $R_5$, $R_6$, $R_7$, $R_8$, $alk_1$, X, $alk_2$, $alk_3$ and $alk_4$ have the meanings given above with the proviso, in compounds of the formula I in which $R_3$ and $R_4$ together are a group —$alk_3$—NH—$alk_4$— and $alk_3$ is ethylene, that, when $alk_4$ is ethylene, $R_1$ is different from unsubstituted phenyl or $R_2$ is different from unsubstituted phenyl and hydrogen and also $R_1$ is different from 2,3,4-trimethoxyphenyl, o-aminodichlorophenyl, o-lower alkanoylaminodichlorophenyl and o-di-lower alkanoylaminodichlorophenyl or $R_2$ is different from hydrogen, and, when $alk_4$ is 1,3-propylene, $R_1$ is different from unsubstituted phenyl or $R_2$ is different from hydrogen, and with the further proviso, in compounds of the formula I in which $R_4$ is a group —$alk_1$—X—$alk_2$—$R_5$ and $R_5$ is a group —N($R_6$)—CH($R_7$)—$R_8$, that, when $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine or at least one of the radicals $R_2$, $R_3$, $R_6$ and $R_7$ is different from hydrogen, wherein, in the case where $R_4$ is a group —$alk_1$—X—$alk_2$—$R_5$ and $alk_1$ and $alk_2$ are methylene and $R_5$ is a group of the formula —N($R_6$)—CH($R_7$)—$R_8$, $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, hydroxy, chlorine, diethylamino and/or dimethylamino when $R_2$, $R_3$, $R_6$ and $R_7$ are hydrogen and X is methylene, or their pharmaceutically acceptable acid addition salts, with the proviso that addition salts with organic carboxylic acids do not have a $\beta$-lactam ring, for use in a method for the therapeutic treatment of the human or animal body, their use for combating diseases or for the manufacture of medicaments and also pharmaceutical preparations containing those salts or compounds.

The invention likewise relates more especially to compounds of the formula I in which $R_1$ and $R_2$ have the meanings given above, $R_3$ is hydrogen or lower alkyl, such as methyl, and $R_4$ is a group of the formula —$alk_1$—X—$alk_2$—N($R_6$)—CH($R_7$)—$R_8$ in which $alk_1$, X, $alk_2$, $R_6$, $R_7$ and $R_8$ have the meanings given above, with the proviso that, in compounds of the formula I in which $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine and from p-hydroxyphenyl when $R_2$, $R_3$, $R_6$ and $R_7$ are hydrogen, and with the further proviso, in compounds of the formula I in which $alk_1$ and $alk_2$ are methylene and X is a direct bond, that, when both radicals $R_2$ and $R_7$ are hydrogen or both are methyl or both are unsubstituted phenyl or $R_2$ is ethyl and $R_7$ is hydrogen, at least one of the radicals $R_1$ and $R_8$ is different from unsubstituted phenyl or at least one of the radicals $R_3$ and $R_6$ is different from hydrogen, wherein $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, hydroxy, chlorine, diethylamino and/or dimethylamino when $R_2$, $R_3$, $R_6$ and $R_7$ are hydrogen and X is methylene, and $R_1$ and $R_8$ are different substituents selected from p-anilino, p-hydroxyphenyl and p-methylphenyl when $R_2$, $R_3$, $R_6$ and $R_7$ are hydrogen and X is a direct bond, and their acid addition salts and processes for their manufacture.

The invention relates especially to the use of compounds of the formula I in which $R_1$ is unsubstituted phenyl or phenyl substituted by lower alkyl, such as methyl, lower alkenyl, such as allyl, 3- to 8-membered cycloalkyl, such as cyclohexyl, lower alkoxy, such as methoxy, lower alkenyloxy, such as allyloxy, lower alkylenedioxy bonded to adjacent carbon atoms, such as ethylenedioxy or 2,2-propylenedioxy, halogen having an atomic number of up to and including 35, such as chlorine, amino and/or by mono- or di-lower alkylamino, such as methyl- or diethyl-amino, $R_2$ is hydrogen or unsubstituted phenyl or phenyl substituted as indicated for $R_1$, $R_3$ is hydrogen or lower alkyl, such as methyl, and $R_4$ is a group of the formula —$alk_1$—X—$alk_2$—$R_5$ or $R_3$ and $R_4$ together are a group of the formula —$alk_3$—NH—$alk_4$—, wherein $alk_1$ and $alk_2$ are lower alkylidene, such as methylene, $alk_3$ and $alk_4$ are lower alkylene, such as ethylene or 1,3-propylene, X is a direct bond, methylene or unsubstituted phenylene, $R_5$ is a group —N($R_6$)—CH($R_7$)—$R_8$, $R_6$ is hydrogen or, provided that $R_3$ is hydrogen, may alternatively be lower alkyl, such as methyl, $R_7$ is hydrogen, lower alkyl, such as methyl, unsubstituted phenyl or phenyl substituted as indicated for $R_1$, lower alkoxycarbonyl, such as methoxy- or ethoxy-carbonyl, or 3- to 8-membered cycloalkoxycarbonyl, such as cyclohexyloxycarbonyl, and $R_8$ is unsubstituted phenyl or phenyl substituted as indicated for $R_1$, and their pharmaceutically acceptable acid addition salts for combating respiratory disorders, for example as the active ingredient in or for the manufacture of medicaments that ease breathing, and also preparations that ease breathing and that contain those compounds or salts.

The invention also relates especially to compounds of the formula I in which $R_1$, $R_2$, $R_3$, $R_4$, $R_5$, $R_6$, $R_7$, $R_8$, $alk_1$, X, $alk_2$, $alk_3$ and $alk_4$ have the meanings given above with the proviso, in compounds of the formula I in which $R_3$ and $R_4$ together are a group —$alk_3$—NH—$alk_4$— and $alk_3$ is ethylene, that, when $alk_4$ is ethylene, $R_1$ is different from unsubstituted phenyl or $R_2$ is different from unsubstituted phenyl and hydrogen and also $R_1$ is different from 2,3,4-trimethoxyphenyl and o-aminodichlorophenyl or $R_2$ is different from hydrogen, and that, when $alk_4$ is 1,3-propylene, $R_1$ is different from unsubstituted phenyl or $R_2$ is different from hydrogen, and with the further proviso, in compounds of the formula I in which $R_4$ is a group —$alk_1$—X—$alk_2$—$R_5$ and $R_5$ is a group —N($R_6$)—CH($R_8$)—$R_7$, that, when $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine or at least one of the radicals $R_2$, $R_3$, $R_6$ and $R_7$ is different from hydrogen, wherein, in the case where $R_4$ is a group —$alk_1$—X—$alk_2$—$R_5$ and $alk_1$ and $alk_2$ are methylene and $R_5$ is a group of the formula —N($R_6$)—CH($R_7$)—$R_8$, $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, chlorine, diethylamino and/or dimethylamino when $R_2$, $R_3$, $R_6$ and $R_7$ are hydrogen and X is methylene, or their pharmaceutically acceptable acid addition salts, with the proviso that addition salts with organic carboxylic acids do not have a $\beta$-lactam ring, for use in a method for the therapeutic treatment of the human or animal body, their use for combating diseases or for the manufacture of medicaments and also pharmaceutical preparations containing those compounds or salts.

The invention likewise relates especially to compounds of the formula I in which $R_1$ and $R_2$ have the meanings given above, $R_3$ is hydrogen or lower alkyl, such as methyl, and $R_4$ is a group of the formula —$alk_1$—X—$alk_2$—N($R_6$)—CH($R_7$)—$R_8$ in which $alk_1$, X, $alk_2$, $R_6$, $R_7$ and $R_8$ have the meanings given above, with the proviso that, in compounds of the formula I in which $alk_1$ and $alk_2$ are methylene and X is methylene or a direct bond, at least one of the radicals $R_1$ and $R_8$ is different from unsubstituted phenyl or phenyl mono- or di-substituted by methoxy and/or chlorine when $R_2$, $R_3$, $R_6$ and $R_7$ are hydrogen, and with the further proviso, in compounds of the formula I in which $alk_1$ and $alk_2$ are methylene and X is a direct bond, that, when both radicals $R_2$ and $R_7$ are hydrogen or both are unsubstituted phenyl at least one of the radicals $R_1$ and $R_8$ is different from unsubstituted phenyl or at least one of the radicals $R_3$ and $R_6$ is different from hydrogen, wherein $R_1$ and $R_8$ are different substituents selected from phenyl radicals that are unsubstituted or mono-, di-, tri- or tetra-substituted in the 3-, 4-, 5- and/or 6-position(s) by isopropyl, methoxy, chlorine, diethylamino and/or dimethylamino when $R_2$, $R_3$, $R_6$ and $R_7$ are hydrogen and X is methylene, and $R_1$ and $R_8$ are different radicals selected from p-anilino and p-methylphenyl when $R_2$, $R_3$, $R_6$ and $R_7$ are hydrogen and X is a direct bond, and their acid addition salts and also processes for their manufacture.

The invention relates most especially to the use of compounds of the formula I in which $R_1$ is unsubstituted phenyl or phenyl substituted by lower alkyl having up to and including 4 carbon atoms, such as methyl, and/or by halogen having an atomic number of up to and including 35, such as chlorine, $R_2$ is hydrogen or unsubstituted phenyl or phenyl substituted as indicated for $R_1$, $R_3$ is hydrogen or lower alkyl having up to and including 4 carbon atoms, such as methyl, and $R_4$ is a group of the formula —$CH_2$—X—$CH_2$—$R_5$ or $R_3$ and $R_4$ together are a group of the formula —$alk_3$—NH—$CH_2CH_2$—, in which X is a direct bond, methylene or unsubstituted phenylene, $R_5$ is amino or substituted amino of the formula —N($R_6$)—CH($R_7$)—$R_8$, $R_6$ is hydrogen or, provided that $R_3$ is hydrogen, it may alternatively be lower alkyl having up to and including 4 carbon atoms, such as methyl, $R_7$ is hydrogen, lower alkyl having up to and including 4 carbon atoms, such as methyl, unsubstituted phenyl or phenyl substituted as indicated for $R_1$ or lower alkoxycarbonyl having up to and including 4 carbon atoms in the alkyl moiety, such as methoxycarbonyl, $R_8$ is unsubstituted phenyl or phenyl substituted as indicated for $R_1$, and $alk_3$ is lower alkylene having from 2 to 4 carbon atoms which separates the two nitrogen atoms by 2 or 3 carbon atoms, such as methylene, ethylene or 1,3-propylene, and their pharmaceutically acceptable acid addition salts for combating respiratory disorders, for example as the active ingredient in or for the manufacture of pharmaceutical preparations, and also medicaments that ease breathing and that contain those compounds or salts.

The invention also relates most especially to compounds of the formula I in which $R_1$, $R_2$, $R_3$, $R_4$, $R_5$, $R_6$, $R_7$, $R_8$, X and $alk_3$ have the meanings given above with the proviso, in compounds in which $R_3$ is hydrogen or lower alkyl having up to and including 4 carbon atoms and R$_4$ is a group of the formula —CH$_2$—X—CH$_2$—N(R$_6$)—CH(R$_7$)—R$_8$, that, when X is methylene or a direct bond, at least one of the radicals R$_1$ and R$_8$ is different from unsubstituted phenyl or phenyl mono- or di-substituted by chlorine or at least one of the radicals R$_2$, R$_3$, R$_6$ and R$_7$ is different from hydrogen, and with the further proviso, in compounds in which R$_3$ and R$_4$ together are a group —alk$_3$—NH—CH$_2$CH$_2$—, that, when alk$_3$ is ethylene, R$_1$ is different from unsubstituted phenyl or R$_2$ is different from unsubstituted phenyl and hydrogen, and, when alk$_4$ is 1,3-propylene, R$_1$ is different from unsubstituted phenyl or R$_2$ is different from hydrogen, wherein R$_1$ and R$_8$ are different substituents selected from phenyl that is unsubstituted or mono-, di-, tri- or tetra-substituted in the 3-, 4-, 5- and/or 6-position(s) by isopropyl and/or chlorine when R$_2$, R$_3$, R$_6$ and R$_7$ are hydrogen and X is methylene, or their pharmaceutically acceptable acid addition salts, with the proviso that addition salts with organic carboxylic acids do not have a β-lactam ring, for use in a method for the therapeutic treatment of the human or animal body, their use for combating diseases or for the manufacture of medicaments and also pharmaceutical preparations containing those compounds or salts.

The invention likewise relates most especially to compounds of the formula I in which R$_1$ and R$_2$ have the meanings given above, R$_3$ is hydrogen or lower alkyl having up to and including 4 carbon atoms, such as methyl, and R$_4$ is a group of the formula —CH$_2$—X—CH$_2$—N(R$_6$)—CH(R$_7$)—R$_8$, wherein X, R$_6$, R$_7$ and R$_8$ have the meanings given above, with the proviso that, when X is methylene or a direct bond, at least one of the radicals R$_1$ and R$_8$ is different from unsubstituted phenyl or phenyl mono- or di-substituted by chlorine or at least one of the radicals R$_2$, R$_3$, R$_6$ and R$_7$ is different from hydrogen, and with the further proviso that, when both radicals R$_2$ and R$_7$ are hydrogen or both are unsubstituted phenyl and X is a direct bond, at least one of the radicals R$_1$ and R$_8$ is different from unsubstituted phenyl or at least one of the radicals R$_3$ and R$_6$ is different from hydrogen, and, when R$_2$, R$_3$, R$_6$ and R$_7$ are hydrogen and X is methylene, at least one of the radicals R$_1$ and R$_8$ is different from p-methylphenyl, wherein R$_1$ and R$_8$ are different substituents selected from phenyl that is unsubstituted or mono-, di-, tri- or tetra-substituted in the 3-, 4-, 5- and/or 6-position(s) by isopropyl and/or chlorine when R$_2$, R$_3$, R$_6$ and R$_7$ are hydrogen and X is methylene, and their acid addition salts, especially pharmaceutically acceptable acid addition salts, and also processes for their manufacture.

The invention relates especially to
N,N'-bis-(diphenylmethyl)-1,3-propylenediamine (I*),
N,N'-bis-(diphenylmethyl)-p-xylylenediamine (II*),
N-diphenylmethyl-N'-(1-phenylethyl)-ethylenediamine (III*),
N-diphenylmethyl-N'-(α-methoxycarbonylbenzyl)-ethylenediamine (IV*),
N,N'-bis-(diphenylmethyl)-1,2-propylenediamine (V*),
N,N'-bis-(diphenylmethyl)-m-xylylenediamine (VI*),
N,N-dibenzyl-N'-diphenylmethyl-ethylenediamine (VII*),
N,N'-di-(o-methylbenzyl)-ethylenediamine (VIII*) and
N,N'-dibenzyl-N-methyl-ethylenediamine (IX*)
and also their salts, especially their pharmaceutically acceptable acid addition salts, especially for use in a method for the therapeutic treatment of the human or animal body, processes for their manufacture, their use as the active ingredients in medicaments or for the manufacture of medicaments, and pharmaceutical preparations containing them, also the use of
N,N'-bis-(diphenylmethyl)-ethylenediamine (X*),
N-diphenylmethyl-ethylenediamine (XI*),
N,N'-di-(p-methylbenzyl)-ethylenediamine (XII*)
and also their pharmaceutically acceptable acid addition salts, with the proviso that addition salts with organic carboxylic acids do not have a β-lactam ring in the anion, for combating diseases, for example for use in a method for the therapeutic treatment of the human or animal body, for example as the active ingredients in medicaments, also the use of
1-diphenylmethyl-piperazine (XIII*),
2-diphenylmethylamino-ethanol (XIV*),
N,N'-dibenzyl-ethylenediamine (XV*),
1-benzyl-piperazine (XVI*),
N,N'-di-(p-chlorobenzyl)-ethylenediamine (XVII*),
N,N'-di-(3,4-dichlorobenzyl)-ethylenediamine (XVIII*),
N,N'-di-(1-phenylethyl)-ethylenediamine (XIX*)
and their pharmaceutically acceptable acid addition salts for combating respiratory disorders, for example as active ingredients in or for the manufacture of medicaments that ease breathing, and also pharmaceutical preparations that ease breathing and that contain those compounds or salts.

The compounds of the formula I can be manufactured according to methods known per se. Thus, novel compounds of the formula I in which R$_4$ is a group of the formula —alk$_1$—X—alk$_2$—N(R$_6$)—CH(R$_7$)—R$_8$ are obtained, for example, by condensing a compound of the formula

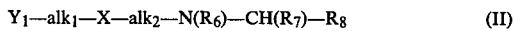
$$Y_1—alk_1—X—alk_2—N(R_6)—CH(R_7)—R_8 \quad (II)$$

with a compound of the formula

$$R_1—CH(R_2)—Y_2 \quad (III)$$

one of the radicals Y$_1$ and Y$_2$ being a nucleophilically replaceable group Y and the other being a group of the formula —N(R$_3$)—H, if necessary separating an isomeric mixture obtainable according to the process into its components and, if desired, converting a compound obtainable according to the process into a different compound of the formula I and/or converting a compound obtainable according to the process into a salt or converting a salt obtainable according to the process into the free compound or into a different salt.

Nucleophilically replaceable groups Y are, for example, reactively esterified hydroxy groups, such as hydroxy groups esterified by an inorganic acid or by an organic sulphonic acid, also ammonium and sulphonium groups. Hydroxy esterified by an inorganic acid is, for example, hydroxy esterified by a hydrohalic acid, for example hydrochloric, hydrobromic or hydriodic acid, and also fluorosulphonyloxy. Hydroxy esterified by an organic sulphonic acid is, for example, aliphatic sulphonyloxy, such as methane-, ethane- and ethenesulphonyloxy, or benzenesulphonyloxy which is unsubstituted or substituted by lower alkyl, halogen and/or nitro, for example benzene-, p-toluene- or p-bromobenzene-sulphonyloxy. Ammonium groups are preferably quaternary ammonium groups, such as tri-lower alkylammonium, for example triethylammonium, or quaternary ammonium groups of heteroaromatic bases, for example, of pyridinium. Sulphonium groups are, for example, di-lower alkylsulphonium groups, for example dimethylsulphonium.

The condensation is carried out in customary manner, for example in the presence of an inert solvent, if necessary in the presence of a condensation agent while cooling or heating and/or under inert gas, such as nitrogen. There come into consideration as condensation agents especially basic condensation agents, such as hydroxides, carbonates or bicarbonates of alkali metals and alkaline earth metals, for example sodium, potassium or calcium hydroxide, or sodium or potassium carbonate, also tertiary organic nitrogen bases, such as tri-lower alkylamines, for example triethylamine, or tertiary nitrogen heteroaromates, for example pyridine or quinoline. The condensation is preferably carried out in a temperature range of approximately from 0° to 120° C., especially at approximately from +10° to +100° C.

The starting materials of the formula II can be manufactured, for example, by condensing a compound of the formula $$Y_1-alk_1-X-alk_2-Y_1' \qquad (IV),$$

in which $Y_1$ is a group $H-N(R_3)-$ and $Y_1'$ is a group $-N(R_6)-H$ and in which the group $-N(R_6)-H$ can be more readily phenalkylated than the group $H-N(R_3)-$, or a salt thereof, with a compound of the formula $$Y_2'-CH(R_7)-R_8 \qquad (V)$$

in which $Y_2'$ is a nucleophilically replaceable radical, for example halogen, preferably in the manner indicated above for the condensation of compounds of the formulae II and III. It is, however, also possible to use as the starting material a compound of the formula IV in which $Y_1$ and $Y_1'$ are nucleophilically replaceable radicals Y, for example halogen, but $Y_1'$ is more reactive than $Y_1$, and this compound can be reacted with a compound of the formula V in which $Y_2'$ is a group $H-N(R_6)-$ and $R_6$ is different from hydrogen. In one process variant which is especially suitable for the manufacture of compounds of the formula II in which $Y_1$ is a group $H-N(R_3)-$ and $R_6$ is the same as $R_3$ and $alk_2$ is the same as $alk_1$, an excess, for example 5 to 10 times the molar amount, of a corresponding diamine of the formula IV ($Y_1=Y_1'=-N(R_3)-H$) is reacted with a halide of the formula V ($Y_2'=$halogen) and the amine excess is separated off.

The intermediates of the formula II obtainable according to one of the above methods of production can be reacted with the reactants of the formula III without being isolated.

Another variant of the above process for the production and further reaction of intermediates of the formula II which is especially suitable for the manufacture of compounds of the formula I in which $R_7$ is the same as $R_2$ and $R_8$ is the same as $R_1$ consists in reacting a compound of the formula IV in which $Y_1$ is a group $H-N(R_3)-$ and $Y_1'$ is a group $-N(R_6)-H$ with double the molar quantity of a compound of the formula III in which $Y_2$ is a nucleophilically replaceable radical Y, for example halogen, or, for the manufacture of compounds of the formula I in which, in addition, $R_6$ is the same as $R_3$, reacting a compound of the formula IV in which $Y_1$ and $Y_1'$ are each a nucleophilically replaceable radical, for example halogen, with double the molar quantity of a compound of the formula III in which $Y_2$ is a group $H-N(R_3)-$.

The novel compounds of the formula I in which $R_4$ is a group of the formula $-alk_1-X-alk_2-N(R_6)-CH(R_7)-R_8$ can also be manufactured by, in a compound of the formula $$R_1-Y_3-X'-Y_4-R_8 \qquad (VI)$$

in which $Y_3$ is a radical $Y_3'$ that can be converted into a group of the formula $-CH(R_2)-N(R_3)-alk_1-$ and $X'$ is a group $X$ or a radical $X''$ that can be converted into methylene or $Y_3$ is a group of the formula $-CH(R_2)-N(R_3)-alk_1-$ and $X'$ is a radical that can be converted into methylene and in which $Y_4$ is a group of the formula $-alk_2-N(R_6)-CH(R_7)-$ or a radical $Y_4'$ that can be converted into that group, or in a salt thereof, converting $Y_3'$ into a group of the formula $-CH(R_2)-N(R_3)-alk_1'-$, $X''$ into methylene and/or $Y_4'$ into a group of the formula $-alk_2-N(R_6)-CH(R_7)-$, if necessary separating an isomeric mixture obtainable according to the process into its components and, if desired, converting a compound obtainable according to the process into a different compound of the formula I and/or converting a free compound obtainable according to the process into a salt or converting a salt obtainable according to the process into the free compound or into a different salt.

There come into consideration as radicals $Y_3'$, for example, those of the formulae $-C(=Y_6)-N(R_3)-alk_1-$, $-CH(R_2)N(R_3)-C(=Y_6)-$, $-C(Y_5)(R_2)-N(R_3)-alk_1-$, $-CH(R_2)-N(R_3)-alk_1'-$, $C(R_2)=N-alk_1-$ and $-CH(R_2)-N=alk''-$, as radicals $X''$, for example, those of the formulae $-CH(Y_5)-$ and $-C(=Y_6)-$ and as radicals $Y_4'$ those of the formulae $-alk_2-N(R_6)-C(=Y_6)-$, $-C(=Y_6)-N(R_6)-CH(R_7)-$, $-alk_2-N(R_6)-C(Y_5)(R_7)-$, $alk_2'-N(R_6)-CH(R_7)-$, $alk_2-N=C(R_7)-$ and $-alk''=N-CH(R_7)-$, in which $Y_5$ is a monovalent and $Y_6$ a divalent radical replaceable by hydrogen, $alk_1'$ and $alk_2'$ are lower alkylidene substituted by at least one radical $Y_5$ and $Y_6$, respectively, and $alk''$ is lower alkylidine. Radicals $Y_5$ are, for example, unmodified or functionally modified hydroxy or mercapto groups, also organic sulphonyl groups and carboxy. Radicals $Y_6$ are, for example, oxo groups or functionally modified oxo groups that are bonded via a double bond.

Functionally modified hydroxy groups are, for example, etherified or esterified hydroxy groups while there come into consideration as functionally modified mercapto groups especially etherified mercapto groups. Etherified hydroxy groups are, for example, lower alkoxy groups, such as methoxy or ethoxy. Esterified hydroxy groups are, for example, hydroxy groups esterified by a mineral acid or an organic carboxylic or sulphonic acid. Organic carboxylic acids are, for example, unsubstituted or substituted benzoic acids or lower alkanecarboxylic acids, for example benzoic or acetic acid. Organic sulphonic acids are, for example, benzene-, p-toluene-, p-bromobenzene-, methane-, ethane- or ethene-sulphonic acid. Mineral acids are preferably hydrohalic acids, for example hydrochloric, hydrobromic or hydriodic acid. Etherified mercapto groups are, for example, lower alkylated or lower alkenylated mercapto groups, such as methylthio, ethylthio or ethylenethio.

Functionally modified oxo groups are, for example, thiono groups, semicarbazono groups or hydrazono groups that are unsubstituted or substituted in the $\beta$- position by organic sulphonyl, such as benzene-, p-toluene-, p-bromobenzene- or methane-sulphonyl.

The conversion of $Y_3'$, $X''$ and, optionally, $Y_4'$, into the groups mentioned is carried out in a manner known per se, for example by reduction, i.e. reaction with a suitable reducing agent. As such there come into consideration, for example: nascent hydrogen, for example hydrogen produced by the action on metals of a compound having labile hydrogen, for example a protonic acid, such as a hydrophalic acid or lower alkanecarboxylic acid, on iron or unamalgamated or amalgamated zinc, magnesium or aluminium, or by the action of water on, preferably amalgamated, aluminium, magnesium or sodium, for example on sodium amalgam, or, for example, hydrogen that is catalytically activated by a hydrogenation catalyst, such as a nickel or noble metal catalyst, for example Raney nickel or platinum that may be in a form that is chemically bonded or bonded to a carrier, for example in the form of an oxide, such as hydrogen catalytically activated by platinum-on-carbon or platinum oxide, or by homogenous noble metal catalysts, such as triphenylphosphineplatinum chloride or triphenylphosphine-rhodium chloride, and there also come into consideration low-valency transition metal compounds, such as tin(II) or chromium(II) salts, for example tin(II) chloride, or hydrides, such as calcium hydride, the boron hydride/tetrahydrofuran complex, or the complex consisting of 9-butyl-9-borabicyclo[3,3,1]nonane and butyllithium, or di-light metal hydrides, such as lithium aluminium hydride, that may be in admixture with aluminium chloride, sodium bis-(2-methoxyethoxy)-aluminium hydride or sodium tris-(2-dimethylaminoethoxy)-aluminium hydride, sodium borohydride, lithium triethyl borohydride or sodium cyanoborohydride in hexamethylphosphoric acid triamide.

The reaction can be carried out in the manner known from the literature to be suitable in each case.

For example, groups $Y_3'$, $X''$ and/or $Y_4'$ having free or esterified or free or etherified hydroxy groups $Y_5$ bonded to a benzylic carbon atom and also having ketonic oxo groups $Y_6$ can be reduced especially by customary reaction with hydrogen that is catalytically activated, for example as indicated above, for example with hydrogen in the presence of palladium-on-carbon, if necessary in an inert solvent, such as a lower alkanol, a lower alkanoic acid or an aliphatic ether, for example in ethanol, acetic acid or dioxan, and/or at elevated temperature.

Radicals $Y_3'$ and/or $Y_4'$ having ketonic oxo groups, sulphonyloxy groups and/or etherified mercapto groups can also be reduced by customary reaction with nascent hydrogen, for example hydrogen produced as indicated above, for example according to Clemmensen's method, preferably with zinc and hydrochloric acid.

Radicals $Y_3'$, $X''$ and/or $Y_4'$ having halogen, free or etherified hydroxy, at least one C—N double bond and/or amidic oxo groups can be reduced, for example, by customary reaction with a suitable di-light metal hydride, such as one of those mentioned, if necessary in an inert solvent and/or at elevated temperature, for example at boiling temperature, starting from halogen compounds, for example with sodium borohydride in water, alcohols, such as ethanol, or ethylene glycol monomethyl ether, or amines, such as pyridine or triethylamine, or with lithium triethyl borohydride, sodium bis-(2-methoxyethoxy)-aluminium hydride in aromatic or araliphatic hydrocarbons, such as benzene or toluene, or with sodium tris-(dimethylaminoethoxy)-aluminium hydride, or starting from lactams or amides, for example with lithium aluminium hydride in an aliphatic ether, for example in diethyl ether, tetrahydrofuran or dioxan, if necessary at boiling temperature.

Radicals $Y_3'$, $X''$ and/or $Y_4'$ having hydrazono groups substituted as indicated, for example β-(p-toluenesulphonyl)-hydrazono, can be replaced by hydrogen especially by customary reaction with a di-light metal hydride, for example with sodium cyanoborohydride in hexamethylphosphoric acid triamide, if necessary at elevated temperature. Radicals $X''$, $Y_3'$ and/or $Y_4'$ having semicarbazono or unsubstituted hydrazono groups can be reduced, for example, by customary reaction with a strong base, for example, according to the Wolff-Kishner method, with an alkali metal alcoholate, for example with sodium methoxide, if necessary under elevated pressure and/or at elevated temperature, or, according to the Huang-Minlon modification, with an alkali metal hydroxide, for example potassium hydroxide, in an inert, high-boiling solvent, for example in di- or tri-ethylene glycol or diethylene glycol monomethyl ether.

Azomethine groups of the formulae $-C(R_2)=N-alk_1-$ and $-CH(R_2)-N=alk''-$ and/or $-alk_2-N=C(R_7)-$ and $-alk''=N-CH(R_7)-$ can be reduced, for example, by catalytically activated hydrogen, such as with hydrogen in the presence of platinum oxide in ethanol at normal or slightly elevated pressure, for example at approximately from 0 to 10 bar overpressure, or with hydrogen in the presence of Raney nickel at elevated pressure, for example at approximately from 20 to 150 bar, preferably approximately 100 bar, overpressure, by reaction with lithium aluminium hydride, preferably in tetrahydrofuran, or by means of nascent hydrogen or by metallic reduction, for example by treatment with zinc and acetic acid, iron and hydrochloric acid and the like.

Starting from azomethine compounds of the formula VI in which $Y_3'$ is a group of the formula $-CH=N-alk_1-$ or $-CH(R_2)-N=alk''-$ and/or $Y_4'$ is a group of the formula $-alk_2-N=CH-$ or $-alk''-=N-CH(R_2)-$, there come into consideration as further reducing agents also lower alkyl metal compounds, and, starting from compounds of the formula VI in which $Y_3'$ is a group of the formula $-CH=N-alk_1-$ and/or $Y_4'$ is a group of the formula $-alk_2N=CH-$, also phenyl metal compounds which may also be substituted by aliphatic and/or cyclo-aliphatic radicals, etherified hydroxy, di-lower alkyl- or lower alkylene-amino and/or trifluoromethyl. "Metal compounds" should in this case be understood as meaning, for example, alkali metal compounds, such as lithium and sodium compounds, and also halo-magnesium compounds, such as bromo-, chloro- or iodo-magnesium compounds. The reaction with such metal compounds is carried out in the customary manner, for example in a di-lower alkyl ether or a lower alkylene ether, for example in diethyl ether, tert-butoxymethane, dioxan or tetrahydrofuran, if necessary while cooling or heating, for example at approximately from 0° to 100° C., and/or under inert gas, such as nitrogen.

In a preferred embodiment of the above process, there is used as starting material, for example, a compound of the formula VI in which $Y_3$ is a group $-C(=O)-N(R_3)-alk_1'-$ or $-CH(R_2)-N(R_3)-C(=O)-$ and $Y_4$ is a group $-alk_2-N(R_6)-CH(R_7)-$, $-alk_2-N(R_6)-C(=O)-$ or $-C(=O)-N(R-$ 6)—CH(R7)— and the oxo group(s) is(are) reduced, for example, by reaction with a suitable di-light metal hydride, for example with lithium aluminium hydride in an ether, for example in diethyl ether or tetrahydrofuran, if necessary at elevated temperature, for example at boiling temperature.

In another preferred embodiment of the above process, there is used as starting material, for example, a compound of the formula VI in which $Y_3$ is a group of the formula —C($R_2$)=N—$alk_1$— and $Y_4$ is a group of the formula —$alk_2$—N($R_6$)—CH($R_7$)— or —$alk_2$—N=C($R_7$)— and the C-N double bond(s) is(are) reduced, for example, by means of hydrogen in the presence of platinum oxide at approximately from 20° to 30° C. and approximately from 0.5 to 1.25 bar, or by reaction with lithium aluminium hydride in tetrahydrofuran, preferably at approximately from 60° C. to boiling temperature.

A further radical $Y_5$ replaceable by hydrogen is the carboxy group which may be in salt form, for example in the form of an alkali metal salt, such as sodium salt, or a copper or ammonium salt. The carboxy group is replaced by hydrogen preferably by decarboxylation, for example by heating to approximately from 100° to 250° C., if necessary in a high-boiling solvent, for example in ethylene glycol, dimethylformamide, ethylene glycol monomethyl ether or diphenylether.

Further radicals that can be converted into groups of the formula —CH($R_2$)—N($R_3$)—$alk_1$— and —$alk_2$—N($R_6$)—CH($R_7$)— in which $R_2$ and $R_6$ are hydrogen are those of the formula —CH($R_2$)N($Y_7$)—$alk_1$— and —$alk_2$—N($Y_7$)—CH($R_7$)—, respectively, in which $Y_7$ is a monovalent radical replaceable by hydrogen. In compounds of the formula VI in which X' is methylene, a direct bond or o-phenylene that is unsubstituted or substituted as indicated, there come into consideration as further radicals that can be converted into the group of the formula —CH($R_2$)—NH—$alk_1$—X'—$alk_2$—NH—CH($R_7$)— those of the formula

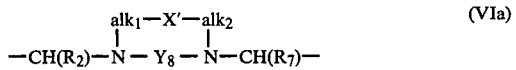 (VIa)

in which $Y_8$ is a divalent radical replaceable by hydrogen.

Monovalent radicals $Y_7$ replaceable by hydrogen are, for example, acyl groups, triarylmethyl groups, 2-acyl-lower alk-1-enyl radicals and silyl groups. Divalent radicals replaceable by hydrogen are, for example, carbonyl and thiocarbonyl groups.

Acyl groups are, for example, acyl groups derived from an organic carboxylic acid having, for example, up to 18 carbon atoms, especially an alkanecarboxylic acid that is unsubstituted or substituted, for example, by halogen or aryl, or benzoic acid that is unsubstituted or substituted, for example, by halogen, lower alkoxy or nitro, or from a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloroacetyl, benzoyl that is unsubstituted or substituted, for example, by halogen, lower alkoxy or nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, arylmethoxycarbonyl having one or two aryl radicals which are preferably phenyl that is unsubstituted or mono- or poly-substituted, for example, by lower alkyl, especially tert-lower alkyl, such as tert-butyl, lower alkoxy, such as methoxy, hydroxy, halogen, for example chlorine, and/or by nitro, such as unsubstituted or substituted benzyloxycarbonyl, for example 4nitrobenzyloxycarbonyl, or substituted diphenylmethoxycarbonyl, aroylmethoxycarbonyl in which the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl in which each of the substituents represents, independently of one another, an aliphatic, araliphatic, cycloaliphatic or aromatic hydrocarbon radical that has, for example, up to 15 carbon atoms and is unsubstituted or substituted, for example, by lower alkyl, lower alkoxy, aryl, halogen or nitro, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further acyl radicals $Y_7$ are also corresponding radicals of organic phosphoric, phosphonic or phosphinic acids, such as di-lower alkylphosphoryl, for example dimethylphosphoryl, diethylphosphoryl, di-n-propylphosphoryl of diisopropylphosphoryl, dicycloalkylphosphoryl, for example dicyclohexylphosphoryl, unsubstituted or substituted diphenylphosphoryl, for example diphenylphosphoryl, diphenyllower alkylphosphoryl that is unsubstituted or substituted, for example, by nitro, for example dibenzylphosphoryl or di-4-nitrobenzylphosphoryl, unsubstituted or substituted phenyloxyphenylphosphonyl, for example phenyloxyphenylphosphonyl, di-lower alkylphosphinyl, for example diethylphosphinyl, or unsubstituted or substituted diphenylphosphinyl, for example diphenylphosphinyl.

In a triarylmethyl group the aryl radicals are especially unsubstituted or substituted phenyl radicals. Such a group is especially trityl.

In a 2-acyl-lower alk-1-en-1-yl radical, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or nitro, or especially of a carbonic acid semiester, such as a carbonic acid lower alkyl semiester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

A silyl group is especially an organic silyl group in which the silicon contains as substituent preferably lower alkyl, especially methyl, also lower alkoxy, for example methoxy, and/or halogen, for example chlorine. Corresponding silyl groups are especially tri-lower alkylsilyl, especially trimethylsilyl, also dimethyl-tert-butyl-silyl, lower alkoxylower alkyl-halo-silyl, for example methoxy-methyl-chlorosilyl, or di-lower alkyl-halo-silyl, for example dimethylchloro-silyl.

Preferred groups $Y_7$ are acyl radicals of carbonic acid semiesters, especially tert-butoxycarbonyl, benzyloxycarbonyl that is unsubstituted or substituted, for example, as indicated, for example 4-nitrobenzyloxycarbonyl, or diphenylmethoxycarbonyl, or 2-halo-lower alkoxycarbonyl, such as 2,2,2-trichloroethoxycarbonyl, also trityl or formyl.

The removal of the mentioned groups $Y_7$ and $Y_8$ is carried out in the customary manner, for example by solvolysis, especially hydrolysis, alcoholysis or ammonolysis or aminolysis, respectively, or by reduction, especially be means of chemical reducing agents.

2-halo-lower alkoxycarbonyl (optionally after converting a 2-bromo-lower alkoxycarbonyl group into a2-iodo-lower alkoxycarbonyl group), aroylmethoxycarbonyl or 4-nitrobenzyloxycarbonyl can be removed, for example, by treatment with a suitable chemical reducing agent, such as zinc in the presence of a suitable carboxylic acid, such as aqueous acetic acid. Aroylmethoxycarbonyl can also be cleaved by treatment with a nucleophilic, preferably salt-forming reagent, such as sodium thiophenolate, and 4-nitrobenzyloxycarbonyl can also be cleaved by treatment with an alkali metal dithionite, for example sodium dithionite. Unsubstituted or substituted diphenylmethoxycarbonyl, tert-lower alkoxycarbonyl or 2-trisubstituted silylethoxycarbonyl can be removed by treatment with a suitable acid, for example formic of trifluoroacetic acid, unsubstituted or substituted benzyloxycarbonyl, for example, by means of hydrogenolysis, i.e. by mild treatment with hydrogen in the presence of a suitable hydrogenation catalyst, such as a palladium catalyst, unsubstituted or substituted triarylmethyl, formyl or 2-acyl-lower alk-1-enyl, for example, by treatment with an acid, such as a mineral acid, for example hydrochloric acid, or an organic acid, for example formic, acetic or trifluoroacetic acid, optionally in the presence of water, and an organic silyl, for example, by means of hydrolysis or alcoholysis. 2-haloacetyl, for example 2-chloroacetyl, can be freed by treatment with thiourea in the presence of a base, or with a thiolate salt, such as an alkali metal thiolate, of thiourea and subsequent solvolysis, such as alcoholysis or hydrolysis, of the resulting condensation product. 2-substituted silylethoxycarbonyl can also be removed by treatment with a salt of hydrofluoric acid yielding fluoride ions, for example with potassium fluoride. A phosphoro, phosphono or phosphino group can be removed, for example, by treatment with a phosphorus-containing acid, such as a phosphoric, phosphonic or phosphinic acid, for example orthophosphoric acid or polyphosphoric acid, an acid ester, for example monomethyl, monoethyl, dimethyl or diethyl phosphate, or monomethylphosphonic acid, or an anhydride thereof, such as phosphorus pentoxide.

The starting materials can be manufactured according to methods known per se.

Thus, compounds of the formula VI in which $Y_3'$ is a group of the formula $-C(=Y_6)-N(R_3)-alk_1-$ are obtained, for example, by condensing with one another according to conventional methods of esteraminolysis, aminoacylation or transamidation compounds of the formulae $$R_1-C(=Y_6)-Z \qquad (VII)$$

and $$H-N(R_3)-alk_1-X'-Y_4-R_8 \qquad (VIII)$$

in which Z is etherified or reactive esterified hydroxy or a quaternary ammonium group, for example lower alkoxy, halogen or pyridinium. Compounds of the formula VIII in which $Y_4$ is a group $-alk_2-N(R_6)-CH(R_7)-R_8$ can for their part be manufactured, for example, by condensing with one another, for example as indicated for the reaction of compounds of the formulae II and III, compounds of the formulae $$Y_1-alk_1-X'-alk_2-Y_1' \qquad (IX)$$

and $$Y_2'-CH(R_7)-R_8 \qquad (V)$$

in which $Y_1$ is a group $H-N(R_3)-$, $Y_1'$ is a nucleophilically replaceable radical Y, for example halogen, and $Y_2'$ is a group $H-N(R_6)-$.

Compounds of the formula VI in which $Y_3'$ is a group $-C(=Y_6)-N(R_3)-alk_1-$ and $Y_4'$ is a group $-alk_2-N(R_6)-C(=Y_6)-$ and in which $R_7$ is the same as $R_2$ and $R_8$ is the same as $R_1$, can be manufactured, for example, by reacting a compound of the formula IX in which $Y_1$ is a group $H-N(R_3)-$and $Y_1'$ is a group $-N(R_6)-H$ with double the molar quantity of a compound of the formula V in which $Y_2'$ is a nucleophilically replaceable radical Y, for example halogen.

Starting from compounds of the formula IX in which $Y_1$ is a group $H-N(R_3)-$ and $Y_1'$ is a group $-N(R_6)-H$ and in which one of these two groups is more readily acylated than the other, it is possible first of all to acylate a more readily acylatable group $H-N(R_3)-$ by reaction with a compound of the formula VII or a more readily acylatable group $-N(R_6)-H$ by reaction with a compound of the formula $$Z-(Y_6=)C-R_8 \qquad (X)$$

and in the resulting compound of the formula IX in which $Y_1$ is a group $R_1-C(=Y_6)-N(R_3)-$ and $Y_1'$ is a group $-N(R_6)-H$, or $Y_1$ is a group $H-N(R_3)-$ and $Y_1'$ is a group $-N(R_6)-C(=Y_6)-R_8$, respectively, to phenalkylate the group $-N(R_6)-H$ or $H-N(R_3)-$ by reaction of the formula V or $$R_1-CH(R_2)-Y_2 \qquad (III),$$

respectively, in which $Y_2'$ or $Y_2$, respectively, is a nucleophilically replaceable radical Y, for example halogen, or to acylate it by reaction with a compound of the formula X or VII, respectively. It is, however, alternatively possible first of all to phenalkylate the more readily phenalkylatable group $H-N(R_3)-$ or $-N(R_6)-H$ by reaction with the compound of the formula III or V, respectively, and then to acylate the primary product by reaction with the compound of the formula X or VII, respectively.

In an analogous manner, starting materials of the formula VI in which $Y_3'$ is a group $-CH(R_2)-N(R_3)-C(=Y_6)-$ and $Y_4'$ is a group $-alk_2-N(R_6)-CH(R_7)-$, $-C(=Y_6)-N(R_6)-CH(R_7)-$ or $-alk_2-N(R_6)-C(=Y_6)-(R_7)-$, are also obtained by reacting a compound of the formula $$Z_1-C(=Y_6)-X'-C(=Y_6)-Z_2 \qquad (XI)$$

in which $Z_1$ and $Z_2$ are, independently of one another, free or etherified or free or reactive esterified hydroxy, such as hydroxy, lower alkoxy or halogen, or, if X' is unsubstituted or substituted o-phenylene and $Y_6$ is oxo, they are together oxy, first of all with an amine of the formula $$R_1\text{—}CH(R_2)\text{—}Y_2 \qquad (III),$$

in which $Y_2$ is —$N(R_3)$—H, and then with an amine of the formula $$Y_2'\text{—}CH(R_7)\text{—}R_8 \qquad (V),$$

in which $Y_2'$ is H—$N(R_6)$—, or reacting a compound of the formula $$Z_1\text{—}C(=Y_6)\text{—}alk_2\text{—}N(R_6)\text{—}H \qquad (XII)$$

first of all with a compound of the formula $$R_1\text{—}CH(R_2)\text{—}Y_2 \qquad (III),$$

in which $Y_2$ is —$N(R_3)$—H, and then with a compound of the formula $$Y_2'\text{—}CH(R_7)\text{—}R_8 \qquad (V),$$

in which $Y_2'$ is a nucleophilically replaceable radical Y, for example halogen, or with a compound of the formula X.

Compounds of the formula VI in which $Y_3$ is a group —C(OH) $(R_2)$—$N(R_3)$—$alk_1$— or —$CH(R_2)$—$N(R_3)$—$alk_1'$—($alk_1'$=α-hydroxy-lower alkylidene) are advantageously manufactured in situ, for example by reacting a compound of the formula VIII under reducing conditions, for example in the presence of formic acid or one of its salts or in the presence of hydrogen activated, for example, by platinum or platinum compounds, preferably in acidic media, for example in acetic acid solution, with a compound of the formula $$(R_1)(R_2)C(=O) \qquad (XIII)$$

or reacting a compound of the formula $$R_1\text{—}CH(R_2)\text{—}Y_2 \qquad (III).$$

in which $Y_2$ is —$N(R_3)$—H with a compound of the formula $$O=alk''\text{—}X'\text{—}Y_4\text{—}R_8 \qquad (XIV)$$

The compound of the formula VI, which is formed as the primary product, is in this case reduced according to the process directly to form the desired end product or, if $R_3$ is hydrogen, via the azomethine ($Y_3$=—$C(R_2)$-=N—$alk_1$— or —$CH(R_2)$—N=$alk_1''$—, respectively).

As an alternative to this process variant, for the manufacture of compounds of the formula I in which $R_7$ is the same as $R_2$ and $R_8$ is the same as $R_1$, a compound of the formula $$Y_1\text{—}alk_1\text{—}X\text{—}alk_2\text{—}Y_2 \qquad (IV),$$

in which $Y_1$ is a group H—$N(R_3)$— and $Y_1'$ is a group —$N(R_6)$—H, can advantageously be reacted with double the molar quantity of a compound of the formula XIII or, for the manufacture of compounds of the formula I in which, in addition, $R_6$, is the same as $R_3$, a compound of the formula $$O=alk''\text{—}X\text{—}alk''=O \qquad (XV)$$

can be reacted with double the molar quantity of a compound of the formula $$R_1\text{—}CH(R_2)\text{—}Y_2 \qquad (III),$$

in which $Y_2$ is H—$N(R_3)$. In this process, an intermediate of the formula VI is formed in which, in the first case, $Y_3$ is a group —$C(OH)(R_2)$—$N(R_3)$—$alk_1$— or, if $R_3$ is H, a group —$C(R_2)$=N—$alk_1$—, and $Y_4$ is a group —$alk_2$—$N(R_3)$—$C(OH)(R_7)$— or, if $R_6$ is H, a group —$alk_2$—N=$C(R_7)$—, or, in the second case, in which $Y_3$ is a group —$CH(R_2)$—$N(R_3)$—$alk_1'$—or, if $R_3$ is H, a group —$CH(R_2)$—N=$alk_1''$ and $Y_4$ is a group —$alk_2'$—N $(R_6)$—$CH(R_7)$— or, if $R_6$ is H, a group —$alk_2''$-=N—$CH(R_7)$—, which intermediate is then reduced according to the process.

Compounds of the formula VI in which $Y_3'$ is a group —$C(R_2)$=N—$alk_1$— or —$CH(R_2)$—N=$alk_1''$— are obtained by condensing, in customary manner, for example in the presence of an acid catalyst, for example p-toluenesulphonic acid, a compound of the formula $$H\text{—}N(R_3)\text{—}alk_1\text{—}X\text{—}Y_4\text{—}R_8 \qquad (VIII),$$

in which $R_3$ is hydrogen, or a salt thereof, with a compound of the formula $$(R_1)(R_2)C(=O) \qquad (XIII)$$

or condensing a compound of the formula $$O=alk_1''\text{—}X\text{—}Y_4\text{—}R_8 \qquad (XIV)$$

with a compound of the formula $$R_1\text{—}CH(R_2)\text{—}Y_2 \qquad (III),$$

in which $Y_2$ is a group —$NH_2$, or with a salt thereof. Compounds of the formula VIII in which $Y_4$ is a group —$alk_2''$=N—$CH(R_7)$— can be obtained, for example, by reacting a compound of the formula $$H_2N\text{—}alk_1\text{—}X\text{—}alk_2''=O \qquad (XVI)$$

with a compound of the formula $$Y_2'\text{—}CH(R_7)\text{—}R_8 \qquad (V),$$

in which $Y_2'$ is amino. Compounds of the formula XIV in which $Y_4$ is a group —$alk_2$—N=$C(R_7)$— can be manufactured in an analogous manner by reacting a compound of the formula $$H_2N\text{—}alk_1\text{—}X\text{—}alk_2'=O \qquad (XVII)$$

with a compound of the formula $$Y_2'\text{—}CH(R_7)\text{—}R_8 \qquad (V),$$

in which $Y_2'$ is amino, and then with a compound of the formula XIII. According to one of these production methods, aromethines of the formula VI can be synthesised in steps. For the manufacture of symmetric aromethines of the formula VI in which $R_7$ is the same as $R_2$ and $R_8$ is the same as $R_1$ practical advantages are obtained, however, by the variant according to which either a compound of the formula $$Y_1\text{—}alk_1\text{—}X\text{—}alk_2\text{—}Y_1' \qquad (IV),$$

in which $Y_1$ and $Y_2$ are amino, or a salt thereof, is reacted with double the molar quantity of a compound of the formula $$(R_1)(R_2)C(=O) \quad (XIII)$$

or a compound of the formula $$O=alk_1-X-alk_2=O \quad (XV)$$

is reacted with double the molar quantity of a compound of the formula $$R_1-CH(R_2)-Y_2 \quad (III),$$

in which $Y_2$ is amino, or with a salt thereof.

Compounds of the formula VI in which X' is a radical X'' of the formula $-CH(Y_5)-$ or $-C(=Y_6)-$ that can be converted into methylene can be manufactured, for example, by condensing with one another, especially in the manner indicated for the reaction of compounds of the formulae II and III, compounds of the formulae $$R_1-CH(R_2)-Y_2 \quad (III)$$

and $$Y_1-alk_1-X''-alk_2-N(R_6)-CH(R_7)-R_8 \quad (XIX)$$

in which one of the radicals $Y_1$ and $Y_2$ is a group $H-N(R_3)$ and the other is a nucleophilically replaceable radical, for example halogen. Compounds of the formula XIX in which $Y_1$ is halogen and X'' is a group $-C(=O)-$ are obtained, for example, by reacting a compound of the formula $$H-alk_1-C(=O)-alk_2-Y \quad (XX)$$

in which Y is a nucleophilically replaceable radical, for example halogen, with a compound of the formula $$Y_2'-CH(R_7)-R_8 \quad (V),$$

in which $Y_2'$ is a group $H-N(R_6)-$ and halogenating the reaction product in the α-position of the group $H-alk_1-$, for example by the action of bromine. Compounds of the formula VI in which $alk_2$ is methylene and X'' is a group $-CH(OH)-$ can be obtained by reacting a compound of the formula $$Y-alk_1-CH\underset{O}{\overset{}{\diagdown\!\!\diagup}}CH_2, \quad (XXI)$$

in which Y is a nucleophilically replaceable radical, for example halogen, first with a compound of the formula $$R_1-CH(R_2)-Y_2 \quad (III)$$

in which $Y_2$ is a group $-N(R_3)-H$ and then with a compound of the formula $$Y_2'-CH(R_7)-R_8 \quad (V),$$

in which $Y_2'$ is a group $H-N(R_6)-$.

For the manufacture of compounds of the formula VI in which X' is a group X'' and in which $R_7$ is the same as $R_2$ and $R_8$ is the same as $R_1$ it is advantageous to combine both production steps by reacting compounds of the formulae $$R_1CH(R_2)-Y_2 \quad (III)$$

and $$Y_1-alk_1-X''-alk_2-Y_1' \quad (XXII)$$

in which $Y_2$ is a radical Y, $Y_1$ is a group $H-N(R_3)-$ and $Y_1'$ is a group $-N(R_6)-H$, or for the manufacture of compounds in which $R_6$ is the same as $R_3$, by reacting compounds of the formulae V and XXII in which $Y_2$ is a group $-N(R_3)-H$ and $Y_1$ and $Y_1'$ are radicals Y, Y being a nucleophilically replaceable radical, such as halogen.

Starting materials of the formula VI in which $Y_3$ is a group of the formula $-CH(R_2)-N(R_3)-alk_1-$, X' is a group X and $Y_4$ is a group of the formula $-alk_2-N(Y_7)-CH(R_7)-$ can be manufactured, for example, by reacting a compound of the formula $$Y_1-alk_1-X-alk_2-Y_1' \quad (IV),$$

in which $Y_1$ is hydroxy and $Y_1'$ is a nucleophilically replaceable radical, for example halogen, with a compound of the formula $$H-N(Y_7)-CH(R_7)-R_8 \quad (XXIII)$$

reactively esterifying the hydroxy group $Y_1$ in the condensation product formed, for example by reaction with thionyl chloride, phosphorus tribromide or an organic sulphonyl chloride, such as p-toluenesulphonyl chloride, and then reacting with a compound of the formula $$R_1-CH(R_2)-Y_2 \quad (III),$$

in which $Y_2$ is a group $-N(R_3)-H$. As an alternative to this process, it is, however, also possible to use as starting materials compounds of the formula IV in which $Y_1$ and $Y_1'$ are nucleophilically replaceable radicals, for example halogen, and in which $alk_1$ is the same as $alk_2$ or $Y_1'$ is more reactive than $Y_1$.

Starting materials of the formula VI in which $Y_3-X'-Y_4$ is a group of the formula VIa can be manufactured, for example, by reacting a compound of the formula $$\underset{H-N-Y_8-N-H,}{\overset{alk_1-X'-alk_2}{\mid\qquad\qquad\mid}} \quad (XXIV)$$

in which $alk_1$ is the same as $alk_2$ first with a compound of the formula V and then with a compound of the formula III in which $Y_2'$ and $Y_2$, respectively, are nucleophilically replaceable radicals, for example halogen.

Compounds obtainable according to the invention can be converted in a manner known per se into different compounds of the formula I in which $R_4$ is a group of the formula $-alk_1-X-alk_2-H(R_6)-CH(R_7)-R_8$.

For example, in a compound obtainable according to the invention in which $R_3$ and $R_6$ are hydrogen, $R_3$ can be replaced by lower alkyl and $R_6$ by lower alkyl or unsubstituted or substituted phenyl-lower alkyl, for example by reaction with a reactive lower alkyl ester or phenyl-lower alkyl ester. Reactive lower alkyl esters are, for example, lower alkyl halides, such as lower alkyl chlorides, bromides or iodides, lower alkylsulphonates, for example lower alkyl-lower alkanesulphonates, such as lower alkyl methanesulphonates or ethanesulphonates, lower alkylbenzenesulphonates, such as lower alkylbenzenesulphonates, lower alkyl-p-toluenesulphonates or -p-bromosulphonates, also lower alkylfluorosulphonates, or di-lower alkyl sulphates. The reaction with the mentioned reactive esters is carried out, for example, in the presence of a basic condensation agent, if necessary in an inert solvent, in vacuo or while heating and/or under inert gas, such as nitrogen. Basic condensation agents are, for example, hydroxides or carbonates of an alkali metal or alkaline earth metal, for example sodium, potassium or calcium hydroxide, sodium or potassium carbonate, or tertiary organic nitrogen bases, such as tri-lower alkylamines, for example triethylamine or diisopropylmethylamine, or heteroaromatic nitrogen bases, for example pyridine. Inert solvents are, for example, lower alkanols, such as methanol, butanol or amyl alcohol, di-lower alkyl ketones, such as acetone, di-lower alkyl ethers or lower alkylene ethers, such as tert-butoxymethane, dioxan or tetrahydrofuran, lower alkanoic acid amides or lactams, such as dimethylformamide or N-methylpyrrolidone, and di-lower alkyl sulphoxides, for example dimethyl sulphoxide, and also mixtures of the same with one another and/or with water. The replacement of hydrogen $R_3$ or $R_6$ by lower alkyl or of hydrogen $R_6$ by phenylalkyl can, however, also be carried out by reaction with a lower alkanal or phenyl-lower alkanal, respectively, in the presence of a reducing agent, for example formic acid or one of its salts.

Furthermore, for example, a free carboxyl group $R_2$ and/or $R_7$ can be converted into an esterified carboxyl group $R_2$ and/or $R_7$ in customary manner, for example by reaction with the corresponding alcohol or a reactive derivative, such as a carboxylic acid ester, phosphorous acid ester, sulphurous acid ester or carbonic acid ester, for example a lower alkanecarboxylic acid ester, tri-lower alkyl phosphite, di-lower alkyl sulphite or the pyrocarbonate of the corresponding alcohol, a diazo-lower alkane, for example with diazomethane, an olefin, such as lower alkene, or an amide acetal, such as a lower alkanecarboxylic acid amide di-lower alkyl acetal, for example with dimethylformamide diethyl acetal.

The reaction with the corresponding alcohol itself is advantageously carried out in the presence of an acid catalyst, such as a protonic acid, for example hydrochloric or hydrobromic acid, sulphuric acid, phosphoric acid, boric acid, benzenesulphonic acid and/or toluenesulphonic acid, or a Lewis acid, for example boron trifluoride etherate, in an inert solvent, especially an excess of the alcohol used and, if necessary, in the presence of a water-binding agent and/or while removing the reaction water by distillation, for example azeotropically, and/or at elevated temperature.

The reaction with a reactive derivative of the corresponding alcohol can be carried out in customary manner starting from a carboxylic, phosphorous, sulphurous or carbonic acid ester, for example in the presence of an acid catalyst, such as one of those mentioned above, in an inert solvent, such as an aromatic hydrocarbon, for example in benzene or toluene, or in an excess of the alcohol derivative used or of the corresponding alcohol. The reaction with amide acetals is advantageously carried out under neutral conditions, for example in acetonitrile or dimethylformamide as the solvent.

The reaction with an olefin can be carried out, for example, in the presence of an acid catalyst, for example a Lewis acid, for example boron trifluoride, a sulphonic acid, for example p-toluenesulphonic acid, or especially of a basic catalyst, for example sodium or potassium hydroxide, advantageously in an inert solvent, such as an ether, for example in diethyl ether or tetrahydrofuran.

The conversions described above of free carboxyl groups into esterified carboxyl groups can, however, alternatively be carried out by first converting in customary manner a compound of the formula I in which $R_2$ and/or $R_7$ are(is) carboxyl into a reactive derivative, preferably starting from a bis-acid addition salt by reaction with a halide of phosphorus or sulphur, for example with phosphorus trichloride or tribromide, phosphorus pentachloride or thionyl chloride, to convert it into an acid halide, or by reaction with a corresponding alcohol or amine to convert it into a reactive ester, i.e. an ester with electron-attracting structures, such as an ester with phenol, thiophenol, p-nitrophenol, 2,4-dinitrophenol or cyanomethyl alcohol, or a reactive amide for example the amide derived from imidazole or 3,5-dimethylpyrazole, and then reacting the resulting reactive derivative with a corresponding alcohol in customary manner, preferably under neutral or acidic conditions.

An esterified carboxyl group $R_2$ and/or $R_7$ can be transesterified in customary manner, for example by reaction with a metal salt, such as the sodium or potassium salt, of a corresponding alcohol or with the alcohol itself in the presence of a catalyst, for example a strong base, for example sodium or potassium hydroxide, or a strong acid, such as a mineral acid, for example hydrochloric acid, sulphuric acid or phosphoric acid, or an organic sulphonic acid, for example p-toluenesulphonic acid, or a Lewis acid, for example boron trifluoride etherate, to form a different esterified carboxyl group.

The novel compounds may, depending on the starting materials and methods chosen, be in the form of one of the possible isomers or a mixture of the same, for example, depending on the number of asymmetric carbon atoms, in the form of pure optical isomers such as antipodes, or in the form of isomeric mixtures, such as racemates, diastereoisomeric mixtures or racemate mixtures.

Because of the physico-chemical differences between their components, diastereoisomeric mixtures and racemate mixtures can be separated in known manner into the pure isomers, diastereoisomers or racemates, for example by chromatography and/or fractional crystallisation.

Resulting racemates can also be resolved into the optical antipodes according to known methods, for example by recrystallisation from an optically active solvent, with the aid of microorganisms, or by reaction with an optically active acid that forms salts with the racemic base, and separation of the salts obtained in this manner, for example on the basis of their different solubilities, into the diastereoisomers from which the antipodes can be freed by the action of suitable agents. Advantageously, the more active of the two antipodes is isolated.

Resulting free compounds of the formula I in which $R_4$ is a group of the formula —alk$_1$—X—alk$_2$—N(R$_6$)—CH(R$_7$)—R$_8$ can be converted into salts in a manner known per se, inter alia by treatment with an acid, or, starting from an acid ($R_2$ and/or $R_7$=carboxy), with a base or with a suitable salt of a carboxylic acid, generally in the presence of a solvent or diluent.

Resulting salts can be converted in a manner known per se into the free compounds, for example by treatment with a basic or acidic reagent, such as an alkali metal hydroxide or a mineral acid, respectively.

The compounds, including their salts, can also be obtained in the form of their hydrates or include the solvent used for crystallisation.

Owing to the close relationship between the novel compounds in free form and in the form of their salts, hereinbefore and hereinafter there shall optionally be understood by free compounds and salts, where appropriate with regard to meaning and purpose, also the corresponding salts and free compounds, respectively.

The invention also relates to those embodiments of the process according to which a compound obtainable as an intermediate at any stage of the process is used as starting material and the remaining process steps are carried out or a starting material is used in the form of a salt and/or racemate or antipode or, especially, is formed under the reaction conditions.

In the process of the present invention, the starting materials used are preferably those that result in the compounds described at the beginning as being especially valuable. The present invention also relates to novel starting materials and processes for their manufacture.

Pharmaceutical preparations that contain one of the compounds of the formula I according to the invention or a pharmaceutically acceptable salt thereof are, for example, those that are intended for enteral, such as oral or rectal, and parenteral, such as intravenous, administration to, and for inhalation by, warm-blooded animals and that contain the pharmacological active ingredient alone or together with a pharmaceutically acceptable carrier. The dosage of the active ingredient depends on the species of the warm-blooded animal, the age and the individual condition, and on the method of adminstration, but also on the molar weight of the active ingredient. For example, there come into consideration for a warm-blooded animal weighing approximately 75 kg daily doses of from approximately 1 to approximately 25, preferably from approximately 4 to approximately 20, especially from approximately 5 to approximately 15, mg (based on the free base), which doses may, if necessary, be divided up into several, for example up to 4, preferably up to 3, individual doses.

The novel pharmaceutical preparations contain, for example, from approximately 1% to approximately 50%, preferably from approximately 4% to approximately 20%, by weight of the active ingredient. Pharmaceutical preparations according to the invention are, for example, those in unit dosage forms, preferably in oral unit dosage form, such as dragées, tablets, capsules or suppositories, also ampoules, preparations in oral unit dosage form containing in each case, for example, from approximately 2 to approximately 25, especially approximately from 5 to 15 mg, of active ingredient.

The pharmaceutical preparations of the present invention are manufactured in a manner known per se, for example by means of conventional mixing, granulating, confectioning, dissolving or lyophilising processes. For example, pharmaceutical prepartions for oral administration can be obtained by combining the active ingredient with solid carriers, optionally granulating a resulting mixture, and processing the mixture or granulate, if desired or necessary after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, for example maize, wheat, rice or potato starch paste, gelatin, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings which are optionally resistant to gastric juices, there being used, inter alia, concentrated sugar solutions, which may contain gum arabic, talc, polyvinylpyrrolidone, polyethylene glycol and/or titanium dioxide, lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colouring substances or pigments may be added to the tablets or dragée coatings, for example for identification or for distinguishing different doses of the active ingredient.

Further orally administrable pharmaceutical preparations are dry-filled capsules made of gelatin, and also soft, sealed capsules made of gelatin and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally with stabilisers. In soft capsules the active ingredient is preferably dissolved or suspended in suitable liquids, such as fatty oils, paraffin oil, or liquid polyethylene glycols, it likewise being possible for stabilisers to be added.

There come into consideration as rectally administrable pharmaceutical preparations, for example, suppositories that consist of a combination of the active ingredient and a suppository base substance. Suitable as a suppository base substance are, for example, natural or synthetic triglycerides, paraffin hydrocarbons, polyethylene glycols or higher alkanols. It is also possible to use gelatin rectal capsules that contain a combination of the active ingredient and a base substance; suitable base substances are, for example, liquid triglycerides, polyethylene glycols or paraffin hydrocarbons.

There are suitable for parenteral administration especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances that increase viscosity, for example sodium carboxymethylcellulose, sorbitol and/or dextran and optionally also stabilisers.

The following Examples illustrate the invention described above; they are not, however, intended to limit in any way the scope thereof. Temperatures are given in Centgrade; pressures are indicated in mbar.

EXAMPLE 1

180 g of N,N'-bis-(diphenylmethylene)-1,2-propylenediamine are dissolved in 540 ml of acetic acid. 3 g of platinum oxide are added and the mixture is scavenged thoroughly with argon and then hydrogen is introduced while stirring vigorously until starting material can no longer be detected by thin layer chromatography (silica gel 60, diethyl ether: $R_f=0.62$) (generally 24 to 48 hours). The reaction solution is diluted with 150 ml of ethanol, the catalyst is filtered off and then the filtrate is concentrated to dryness by evaporation under reduced pressure in a water bath. The oil residue obtained after concentration by evaporation is triturated with 375 ml of 10% sodium hydroxide solution and extracted twice with 375 ml of diethyl ether each time. The ether phases are combined, washed twice with 70 ml of saturated sodium chloride solution each time, dried over magnesium sulphate and then evaporated to dryness on a water bath, first at approximately 20 mbar and then at approximately 0.03 mbar. The residue is dissolved in approximately 300 ml of ethanol, water is added until the solution starts to become cloudy (approximately 20 ml) and then the whole is caused to crystallise in an ice bath. The precipitated crystals are filtered with suction, washed with a little methanol and dried thoroughly at approximately 0.03 mbar. N,N'-bis-(diphenylmethyl)-1,2-propylenediamine having a melting point of 72°–75° C. is obtained which can be further purified by recrystallisation from approximately double the quantity of methanol and by precipitation with water, and then melts at 75°–77° C.

The starting material can be manufactured, for example, as follows:

255.1 g of benzophenone, 298 ml of 1,2-diaminopropane and 0.2 g of p-toluenesulphonic acid are mixed and heated for 30 minutes under reflux. Approximately 250 ml are then distilled off, the remainder is allowed to cool to approximately 80° C. and approximately 350 ml of 2-ethoxyethanol (ethylene glycol monoethyl ether) are added, followed, while stirring, by 70 ml of water and the whole is allowed to crystallise in an ice bath. N,N'-bis-(diphenylmethylene)-1,2-propylenediamine is obtained which can be purified by recrystallisation from ethanol (approximately 180 ml) and should be dried thoroughly before further reaction.

In an analogous manner, there are obtained, starting from benzophenone, by reaction with m-xylylenediamine via N,N'-bis-(diphenylmethylene)-m-xylylenediamine, N,N'-bis-(diphenylmethyl)-m-xylylenediamine, m.p. 89°–90° C. (from isopropanol), by reaction with 1,3-propylenediamine via N,N'-bis-(diphenylmethylene)-1,3-propylenediamine, N,N'-bis-(diphenylmethyl)-1,3-propylenediamine, m.p. 83°–84° C. (from acetone), and by reaction with p-xylylenediamine via N,N'-bis-(diphenylmethylene)-p-xylylenediamine, N,N'-bis-(diphenylmethyl)-p-xylylenediamine, m.p. 92°–94° C. (from diethyl ether).

EXAMPLE 2

20.2 g of triethylamine, 7.4 g of N-methyl-ethylenediamine and 25.2 g of benzyl chloride are added in succession, while stirring, to 240 ml of acetonitrile; the mixture is boiled under reflux for approximately 48 hours and the precipitated triethylammonium chloride is filtered off. The filtrate is concentrated by evaporation under reduced pressure. The oily residue is taken up in 100 ml of diethyl ether and extracted by shaking with 50 ml of 10% sodium hydroxide solution. The aqueous phase is washed with 100 ml of ether. The ether phases are combined, washed twice with 50 ml of saturated sodium chloride solution each time, dried over magnesium sulphate and concentrated to dryness by evaporation under mild conditions. The residue obtained after concentration by evaporation is distilled under reduced pressure (under 0.1 mbar). N,N'-dibenzyl-N-methyl-ethylenediamine is obtained having a $b.p._{0.028}=123°$ C.

In an analogous manner it is also possible to obtain: by reaction of ethylenediamine with o-methylbenzyl chloride, N,N'-di-(o-methylbenzyl)-ethylenediamine, m.p. 38°–39° C., and by reaction of 1,2- or 1,3-propylenediamine or m- or p-xylylenediamine with benzhydryl chloride, N,N'-bis-(diphenylmethyl)-1,2-propylenediamine, m.p. 75°–77° C. (from methanol/water), N,N'-bis-(diphenylmethyl)-1,3-propylenediamine, m.p. 83°–84° C. (from acetone), N,N'-bis-(diphenylmethyl)-m-xylylenediamine, m.p. 89°–90° C. (from isopropanol) and N,N'-bis-(diphenylmethyl)-p-xylylenediamine, m.p. 92°–94° C. (from diethyl ether), respectively.

EXAMPLE 3

5.3 g of N,N'-di-(o-methylbenzylidene)-ethylenediamine, dissolved in 75 ml of tetrahydrofuran, are added dropwise to a suspension of 2.0 g of lithium aluminium hydride in 30 ml of tetrahydrofuran. The mixture is heated under reflux for 30 minutes, the excess of reducing agent is decomposed with water while cooling with ice, the whole is poured into 200 ml of sodium hydroxide solution (10% by weight) and extracted 3 times by shaking with 150 ml of diethyl ether each time. From the combined diethyl ether extracts the hydrochloride is precipitated, in form of a white powder, by adding a solution of hydrogen chloride in diethyl ether. The hydrochloride is separated by filtration, shaken with 150 ml of diethyl ether and 150 ml of 10% sodium hydroxide solution. The ether phase is dried over magnesium sulphate and concentrated to dryness by evaporation. The residue is recrystallised from ethyl acetate. N,N'-di-(o-methylbenzyl)-ethylenediamine having a meltinp point of 38°–39° C. is obtained.

The starting material can be manufactured, for example, as follows:

A mixture of 24 g of 2-methylbenzaldehyde, 200 ml of toluene and 5.8 g of ethylenediamine is stirred overnight. Approximately 125 ml are then distilled off under reduced pressure. The precipitated N,N'-di-(o-methylbenzylidene)-ethylenediamine is filtered with suction. It melts at 51°–52° C.

EXAMPLE 4

6.15 g of N,N'-dibenzyl-N-methyl-ethylenediamine are dissolved in 60 ml of diethyl ether. Hydrogen chloride is then introduced while stirring and cooling (if necessary in an acetone/dry-ice bath) until a sample, dried on a clay plate, melts at 227°–229° C. The precipitated product is filtered with suction, washed with ether and dried to constant weight under reduced pressure (under 0.1 mbar). N,N'-dibenzyl-N-methyl-ethylenediamine dihydrochloride is obtained, m.p. 227°–229° C.

EXAMPLE 5

A solution of 9.2 g of α-chlorophenylacetic acid methyl ester, dissolved in 10 ml of acetonitrile, is added dropwise in the course of 10 minutes, while stirring, to a mixture of 11.3 g of N-diphenylmethyl-ethylenediamine; 5.05 g of triethylamine and 70 ml of acetonitrile. The mixture is then heated under reflux for 18 hours. It is then concentrated to dryness by evaporation under reduced pressure, triturated with 100 ml of 10% sodium hydroxide solution and extracted twice by shaking with 100 ml of diethyl ether each time. The ether phases are combined, washed three times with 30 ml of saturated sodium chloride solution each time, dried over magnesium sulphate and concentrated by evaporation. The residue obtained after concentration by evaporation is shaken with 10% (by weight) sodium hydroxide solution and diethyl ether in order to remove any excess triethylamine. The ether phases are further treated as indicated above. Finally, drying is effected at approximately 0.15 mbar. N-(α-methoxycarbonylbenzyl)-N'-diphenylmethyl-ethylenediamine is obtained which is converted into the diacetate for characterisation. For that purpose, 14.8 g of base are dissolved in 15 ml of diethyl ether and 15 ml of hexane, and glacial acetic acid is added dropwise while stirring and cooling. The precipitate is filtered with suction, recrystallised from approximately 360 ml of diethyl ether and 90 ml of hexane and dried under reduced pressure (under 0.2 mbar). The N-(α-methoxycarbonylbenzyl)-N'-diphenylmethyl-ethylenediamine acetate melts at 78°–81° C. Pure N-(α-methoxycarbonylbenzyl)-N'-diphenylmethyl-ethylenediamine can be freed from this by treatment with 10% sodium hydroxide solution, extraction by shaking with diethyl ether, drying over magnesium sulphate and evaporating off the solvent.

The N-diphenylmethyl-ethylenediamine used as starting material can be manufactured, for example, as follows:

A mixture of 90.15 g of ethylenediamine, 50.7 g of benzhydryl chloride and 300 ml of acetonitrile is heated under reflux for 24 hours. It is partitioned between 400 ml of diethyl ether and 175 ml of 10% sodium hydroxide solution, the ether phase is separated off, dried over magnesium sulphate, evaporated to dryness and distilled under reduced pressure. N-diphenylmethyl-ethylenediamine is obtained, b.p._{0.13}=116°–124° C., m.p. 23°–24° C.

The α-chlorophenylacetic acid methyl ester used as the starting material can be manufactured, for example, as follows:

16 g of methanol are added dropwise while stirring to 94.5 g of α-chlorophenylacetyl chloride. 5 drops of concentrated sulphuric acid are added, the mixture is boiled for 2 hours while stirring, allowed to cool and poured onto 150 ml of ice water. The organic phase is separated off and the aqueous phase is extracted twice by shaking with 50 ml of diethyl ether each time. The organic phases are combined, neutralised with 50 ml of saturated potassium carbonate solution, washed with 50 ml of water, dried over sodium sulphate and concentrated by evaporation under reduced pressure. The residue obtained after concentration by evaporation is distilled under reduced pressure (under 0.2 mbar). The α-chlorophenylacetic acid methyl ester boils under 0.13 mbar at 62° C.; ($n_D^{20}$: 1.5268).

In an analogous manner, there can be obtained by reaction of N-diphenylmethylethylenediamine with benzyl chloride or 1-phenylethyl chloride, N,N-dibenzyl-N'-diphenylmethylethylenediamine, m.p. 89°–91° C. (from diisopropyl ether), and N-diphenylmethyl-N'-(1-phenylethyl)-ethylenediamine, m.p. of the dihydrochloride 160° C. (with decomposition), respectively.

EXAMPLE 6

85 ml of 10% sodium hydroxide solution are added to 8.5 g of N-(α-methoxycarbonylbenzyl)-N'-diphenylmethylethylenediamine diacetate and the mixture is extracted three times by shaking with 85 ml of diethyl ether each time. The ether solutions of the N-(α-methoxycarbonylbenzyl)-N'-diphenylmethyle-thylenediamine are combined and dried over magnesium sulphate. Hydrogen chloride is then introduced while cooling well (if necessary in an acetone/dry-ice bath) until the base has completely precipitated as the dihydrochloride. The salt is filtered with suction, washed several times with ether and dried to constant weight under reduced pressure (under 0.1 mbar). N-(α-methoxycarbonylbenzyl)-N'-diphenylmethyl-ethylenediamine dihydrochloride having a melting point of 148° C. (with decomposition) is obtained.

EXAMPLE 7

A mixture of 18.3 g of benzhydrylamine, 10 g of triethylamine and 60 ml of acetonitrile is added dropwise to a boiling mixture of 13.2 g of 1,4-bis-(bromomethyl)-benzene in 60 ml of acetonitrile. The mixture is left to boil overnight, is greatly concentrated, and partitioned between 200 ml of ether and 200 ml of 10% sodium hydroxide solution, concentrated by evaporation and recrystallised from diethyl ether. N,N'-bis-(diphenylmethyl)-p-xylylenediamine having a melting point of 92°–94° C. is obtained.

In an analogous manner thare are obtained by reaction of o-methylbenzylamine with 1,2-dibromoethane, N,N'-di-(o-methylbenzyl)-ethylenediamine, m.p. 38°–39° C. (from ethyl acetate), and by reaction of benzhydrylamine with 1,2- or 1,3-dibromopropane or 1,3-bis-(bromomethyl)-benzene, N,N'-bis-(diphenylmethyl)-1,2-propylenediamine, m.p. 75°–77° C. (from methanol/water), N,N'-bis-(diphenylmethyl)-1,3-propylenediamine, m.p. 83°–84° C. (from acetone) and N,N'-bis-(diphenylmethyl)-m-xylylenediamine, m.p. 89°–90° C. (from isopropanol), respectively.

EXAMPLE 8

11 g of N-diphenylmethyl-ethylenediamine, 10.1 g of triethylamine and 7.0 g of 1-phenylethyl chloride are dissolved, while stirring, in 85 ml of acetonitrile and heated under reflux for 30 hours. The solution is concentrated by evaporation under reduced pressure, 50 ml of 10% sodium hydroxide solution are added and the mixture is extracted thoroughly by shaking with diethyl ether. The ether extracts are combined, dried over sodium sulphate and concentrated by evaporation. N-diphenylmethyl-N'-(1-phenylethyl)-ethylenediamine is obtained in the form of a yellow oil which can be purified chromatographically over silica gel with methanol/ethyl acetate (1:1) as the eluant and, for characterisation, can be converted into the dihydrochloride, having a melting point of 160° C., as described in Example 4.

EXAMPLE 9

A solution of 2.9 g of benzyl chloride in 25 ml of acetonitrile is added to 5.6 g of N-diphenylmethyl-ethylenediamine in 30 ml of boiling acetonitrile. The mixture is heated under reflux for 12 hours, concentrated and partitioned between diethyl ether and 10% sodium hydroxide solution. The organic phases are dried over sodium sulphate and concentrated by evaporation. The residue can be recrystallised from methanol or diisopropyl ether. N,N-dibenzyl-N'-diphenylmethyl-ethylenediamine having a melting point of 89°–91° C. is obtained.

EXAMPLE 10

25 g of N,N'-bis-(diphenylmethyl)-1,2-propylenediamine dissolved in 75 ml of methanol are added dropwise while stirring vigorously at 10° C. to a solution of 12.05 g of methanesulphonic acid in 175 ml of water. The mixture is stirred for a further 15 minutes at room temperature, inoculated and left to crystallise overnight. The methanol is then drawn off under reduced pressure and the remainder is left to crystallise completely at 0° C., is filtered with suction, washed with 40 ml of ice water and left to dry under 0.1 to 0.4 mbar, first for a few hours at room temperature and then overnight at 50° C. N,N'-bis-(diphenylmethyl)-1,2-propylenediamine bis-methanesulphonate having a melting point of 218°–219° C. (with decomposition) is obtained.

EXAMPLE 11

Tablets containing 5 mg of N,N'-bis-(diphenylmethyl)-1,2-propylenediamine bis-methanesulphonate can be obtained, for example, as follows:

| Composition: (for 10,000 tablets): | |
|---|---|
| active ingredient | 50 g |
| lactose | 460 g |
| maize starch | 450 g |
| polyvinylpyrrolidone | 20 g |
| magnesium stearate | 10 g |
| colloidal silica | 10 g |
| water | q.s. |

The active ingredient, the lactose and 400 g of the maize starch are mixed and moistened with an aqueous solution of polyvinylpyrrolidone. The mixture is granulated and dried and the magnesium stearate, the colloidal silica and the maize starch left over are added. The mixture is forced through a sieve, mixed and pressed to form tablets weighing 100 mg (diameter: 6 mm).

EXAMPLE 12

Tablets containing 20 mg of N,N'-bis-(diphenylmethyl-1,2-propylenediamine bis-methanesulphonate (active ingredient) can be manufactured, for example, in the following composition:

| Composition: (for 10,000 tablets): | |
|---|---|
| active ingredient | 200 g |
| lactose | 500 g |
| wheat starch | 773 g |
| colloidal silica | 13 g |
| talc | 12 g |
| magnesium stearate | 2 g |

Manufacture

The active ingredient is mixed with lactose, part of the wheat starch and with the colloidal silica and the mixture is forced through a sieve. A further part of the wheat starch is made into a paste with 5 times the quantity of water on a water bath and the powder mixture is kneaded with this paste until a slightly plastic substance has been formed. This substance is forced through a sieve having a mesh width of approximately 1 mm, dried and the dry granulate is again forced through a sieve. The remaining wheat starch, the talc and the magnesium stearate are then admixed. The resulting tablet mixture is pressed to form tablets each weighing 150 mg and having a breaking notch.

EXAMPLE 13

Tablets containing 10 mg of N,N'-bis-(diphenylmethyl)-1,2-propylenediamine bis-methanesulphonate (active ingredient) can be manufactured, for example, in the following composition:

| Composition: (for 10,000 tablets): | |
|---|---|
| active ingredient | 100 g |
| wheat starch | 295 g |
| lactose | 500 g |
| colloidal silica | 50 g |
| talc | 50 g |
| magnesium stearate | 5 g |

Manufacture

The active ingredient is mixed with part of the wheat starch, with the lactose and the colloidal silica and the mixture is forced through a sieve. A further part of the wheat starch is made into a paste with 5 times the quantity of water on a water bath and the powder mixture is kneaded with this paste until a slightly plastic substance has been formed.

The plastic substance is pressed through a sieve having a mesh width of approximately 3 mm, dried and the dry granulate is again forced through a sieve. The remaining wheat starch, the talc and the magnesium stearate are admixed and the resulting mixture is pressed to form tablets weighing 100 mg (with a breaking notch).

EXAMPLE 14

Capsules having a content of 10 mg of N,N'-bis-(diphenylmethyl)-1,2-propylenediamine bis-methanesulphonate (active ingredient) are manufactured, for example, as follows:

| Ingredients: (for 10,000 capsules): | |
|---|---|
| active ingredient | 100 g |
| lactose | 360 g |
| magnesium stearate | 40 g |

The ingredients are mixed in a suitable mixer, forced through a No. 40 sieve and mixed again. Each 0.05 g of the mixture is introduced into a gelatin capsule No. 3.

EXAMPLE 15

In a manner analogous to that described in Examples 11 to 14, it is also possible to manufacture pharmaceutical preparations containing one of the compounds of the formula I mentioned in Examples 1 to 9 or in the description.

I claim:

1. A method of easing the breathing activity of a warm-blooded organism suffering from respiratory disorders or being exposed to unfavourable respiratory conditions, comprising administering to the organism a breathing effectively easing amount of a compound of the formula $$R_1-CH(R_2)-N(R_3)-R_4 \qquad (IC)$$

in which $R_3$ is hydrogen, methyl or benzyl, and

R₄ is: the group —alk₁—X—alk₂—R₅, or

R₃ and R₄ together are the group —alk₃—NH—alk₄ wherein:

alk₁ and alk₂ are the same or different and are each lower alkylidene, alk₃ and alk₄ are the same or different and are each ethylene X is a direct bond, methylene or phenylene, R₅ is: hydroxy, amino, or the group

—N(R₆)—CH(R₇)—R₈;

each of R₁ and R₈ being the same or a different one of the groups: phenyl or phenyl substituted by one of the substituents: methyl and halogen having an atomic number of at most 35, any such halogen substituent being in positions meta- or para- of the phenyl nucleus, R₆ is hydrogen or lower alkyl, but at least one of R₃ and R₆ must be hydrogen;

R₂ and R₇ are the same or different and are each one of the following: hydrogen, lower alkyl, phenyl, phenyl substituted as defined for R₁, lower alkoxycarbonyl of from 2 to 5 carbon atoms; and groups defined as "lower alkyl" hereinbefore having at most 7 carbon atoms;

or of a pharmaceutically acceptable salt of the compound of Formula IC.

2. The method of claim 1, wherein said compound of Formula IC is N,N'-bis-(diphenylmethyl)-1,3-propylenediamine.

3. The method of claim 1, wherein said compound of Formula IC is N,N'-bis-(diphenylmethyl)-p-xylylenediamine.

4. The method of claim 1, wherein said compound of Formula IC is N-diphenylmethyl-N'-(1-phenylethyl)-ethylenediamine.

5. The method of claim 1, wherein said compound of Formula IC is N-diphenylmethyl-N'-(α-methoxycarbonylbenzyl)-ethylenediamine.

6. The method of claim 1, wherein said compound of Formula IC is N,N'-bis-(diphenylmethyl)-m-xylylenediamine.

7. The method of claim 1, wherein said compound of Formula IC is N,N-dibenzyl-N'-diphenylmethyl-ethylenediamine.

8. The method of claim 1, wherein said compound of Formula IC is N,N'-di-(o-methylbenzyl)-ethylenediamine.

9. The method of claim 1, wherein said compound of Formula IC is N,N'-dibenzyl-N-methyl-ethylenediamine.

10. The method of claim 1, wherein said compound of Formula IC is N,N'-bis-(diphenylmethyl)-ethylenediamine.

11. The method of claim 1, wherein said compound of Formula IC is N-diphenylmethyl-ethylenediamine.

12. The method of claim 1, wherein said compound of Formula IC is N,N'-di-(p-methylbenzyl)-ethylenediamine.

13. The method of claim 1, wherein 1-diphenylmethyl-piperazine or a pharmaceutically acceptable salt thereof is used as the active ingredient.

14. The method of claim 1, wherein 2-diphenylmethylamino-ethanol or a pharmaceutically acceptable salt thereof, is used as the active ingredient.

15. The method of claim 1, wherein N,N'-dibenzylethylenediamine or a pharmaceutically acceptable salt thereof is used as the active ingredient.

16. The method of claim 1, wherein 1-benzyl-piperazine or a pharmaceutically acceptable salt thereof is used as the active ingredient.

17. The method of claim 1, wherein N,N'-di-(p-chlorobenzyl)-ethylendiamine or a pharmaceutically acceptable salt thereof is used as the active ingredient.

18. The method of claim 1, wherein N,N'-di-(3,4-dichlorobenzyl)-ethylenediamine or a pharmaceutically acceptable salt thereof is used as the active ingredient.

19. The method of claim 1, wherein N,N'-di-(1-phenylethyl)-ethylenediamine or a pharmaceutically acceptable salt thereof is used as the active ingredient.

20. The method of claim 1, wherein N,N'-bis-(diphenylmethyl)-1,2-propylenediamine or a pharmaceutically acceptable salt thereof is used as the active ingredient.

21. A method according to claim 1, wherein a pharmaceutical preparation according to either one of claims 16 and 17 is administered.

* * * * *